United States Patent
Komatsu et al.

(10) Patent No.: US 7,038,039 B2
(45) Date of Patent: May 2, 2006

(54) PROCESS FOR SELECTIVELY PRODUCING 1-PHOSPHORYLATED SUGAR DERIVATIVE ANOMER AND PROCESS FOR PRODUCING NUCLEOSIDE

(75) Inventors: Hironori Komatsu, Chiba (JP); Hirokazu Awano, Chiba (JP); Nobuyuki Fukazawa, Chiba (JP); Kiyoshi Ito, Chiba (JP); Ichirou Ikeda, Chiba (JP); Tadashi Araki, Chiba (JP); Takeshi Nakamura, Chiba (JP); Tamotsu Asano, Chiba (JP); Junya Fujiwara, Chiba (JP); Tomoyuki Ando, Chiba (JP); Katsutoshi Tsuchiya, Chiba (JP); Kyoko Maruyama, Chiba (JP); Hideki Umetani, Chiba (JP); Takahiro Yamauchi, Chiba (JP); Hitoki Miyake, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/958,305

(22) PCT Filed: Feb. 13, 2001

(86) PCT No.: PCT/JP01/00968

§ 371 (c)(1),
(2), (4) Date: May 7, 2002

(87) PCT Pub. No.: WO01/58920

PCT Pub. Date: Aug. 16, 2001

(65) Prior Publication Data
US 2002/0193314 A1   Dec. 19, 2002

(30) Foreign Application Priority Data

| Feb. 10, 2000 | (JP) | ............................. 2000-033212 |
| Mar. 10, 2000 | (JP) | ............................. 2000-067333 |
| Nov. 9, 2000 | (JP) | ............................. 2000-341960 |

(51) Int. Cl.
*A61K 31/665* (2006.01)
*A61K 31/7024* (2006.01)
*C07F 9/6544* (2006.01)

(52) U.S. Cl. .................. 536/117; 536/124; 536/26.7; 536/27.11; 536/55.3; 536/18.5; 536/22.1; 514/45; 514/23; 514/79; 514/90; 514/99; 544/53; 544/97; 544/244; 549/5; 435/88; 435/87; 435/89; 435/193; 435/72

(58) Field of Classification Search ................ 536/117, 536/26.7, 27.11, 55.3, 124, 18.5, 22.1; 514/45, 514/23, 79, 90, 99; 544/53, 97, 244; 549/5; 435/88, 87, 89, 193, 72
See application file for complete search history.

(56) References Cited

U.S. PATENT DOCUMENTS

| 3,872,085 | A |   | 3/1975 | Penasse et al. |
| 4,476,301 | A |   | 10/1984 | Imbach et al. |
| 4,698,331 | A |   | 10/1987 | Macher et al. |
| 4,853,386 | A |   | 8/1989 | Friebe et al. |
| 4,904,666 | A |   | 2/1990 | Friebe et al. |
| 5,371,203 | A |   | 12/1994 | Schmidt et al. |
| 5,674,998 | A |   | 10/1997 | Boyer et al. |
| 5,770,407 | A | * | 6/1998 | Wong et al. .................. 435/89 |
| 5,792,840 | A |   | 8/1998 | Shiozaki et al. |
| 5,922,867 | A |   | 7/1999 | Mansour et al. |
| 6,017,736 | A | * | 1/2000 | Mikami et al. ............... 435/88 |
| 6,620,596 | B1 | * | 9/2003 | Mikami et al. ............... 435/88 |

FOREIGN PATENT DOCUMENTS

| DE | 38 34 877 A1 | 5/1990 |
| DE | 197 40 357 A1 | 3/1999 |
| EP | 0 287 907 A1 | 4/1988 |
| EP | 0 309 411 A2 | 3/1989 |
| EP | 0 502 298 A2 | 1/1992 |
| EP | 0 561 523 A2 | 9/1993 |
| JP | 62-45588 A | 2/1987 |
| JP | 63-258880 A | 10/1988 |
| JP | 4-312598 A | 4/1992 |
| JP | 09-224691 | 9/1997 |
| JP | 11-507387 A | 6/1999 |
| WO | 92/08717 A1 | 5/1992 |
| WO | 95/29176 A1 | 11/1995 |
| WO | 96/40705 A1 | 12/1996 |
| WO | 98/25940 A1 | 6/1998 |
| WO | 02/31176 A1 | 4/2002 |
| WO | 02/051852 A1 | 7/2002 |

OTHER PUBLICATIONS

Perchemlides et al. "Synthesis of alpha-L-idopyranosyl, (alpha-L-idopyranosyluronic acid),alpha-D-mannopyranosyl, and alpha D-mannopyranosyluronic acid) phsphates." Carbohydrate Res. 3, 463-477, 1967.*

(Continued)

*Primary Examiner*—James O. Wilson
*Assistant Examiner*—Devesh Khare
(74) *Attorney, Agent, or Firm*—Buchanan Ingersoll PC

(57) ABSTRACT

A desired isomer is selectively prepared by phosphorolyzing and isomerizing an anomer mixture of a 1-phosphorylated saccharide derivative while crystallizing one of the isomers to displace the equilibrium. Furthermore, using the action of a nucleoside phosphorylase, a nucleoside is prepared from the 1-phosphorylated saccharide derivative obtained and a base with improved stereoselectivity and a higher yield. This process is an anomer-selective process for preparing a 1-phosphorylated saccharide derivative and a nucleoside.

26 Claims, No Drawings

OTHER PUBLICATIONS

Thomas A. Krenitsky et al., "Purine Nucleoside Synthesis, an Efficient Method Employing Nucleoside Phosphorylases," 20 Biochemistry 3615-3621 (1981).

Prihar, Harry S. et al., "Synthesis of β-L-Fucopyranosyl Phosphate and L-Fucofuranosyl Phosphates by the MacDonald Procedure," Carbohydrate Research, (1977) 56 (2), pp. 315-324 (XP-009008231).

Maryanoff, Bruce E. et al., "Synthesis of Phosphates and Phosphate Isoteres of Furanose Sugars as Potential Enzyme Inhibitors," Tetrahedron, (1988), vol. 44, No. 11, pp. 3093-3106 (XP-001146722).

Halmann, M. et al., "Phosphorylation of D-Ribose in Aqueous Solution," The Journal of Organic Chemistry, (1969), vol. 34, No. 11, pp. 3702-3703 (XP-002236090).

Komatsu, Hironori et al., "First Stereoselective Synthesis of 2-Deoxy-α-D-ribosyl-1-phosphate: Novel Application of Crystallization-Induced Asymmetric Transformation," Journal of Organic Chemistry, (2002), vol. 67, No. 15, pp. 5419-5421 (XP-002236091).

Komatsu, Hironori et al., "Large-Scale Manufacturing of All Four 2'-Deoxynucleosides Via Novel Strategies Including a Chemo-Enzymatic Process," Nucleosides, Nucleotides & Nucleic Acids, (2001), 20(4-7), 1291-1293 (XP009008095).

Mascia, Laura et al., "Ribose 1-phosphate and inosine activate uracil salvage in rat brain", Biochim. Biophys. Acta. (1999), vol. 1472 No. 1-2, pp. 93-98.

Giorgelli, Francesco et al., "Recycling of α-D-ribose 1-phosphate for nucleoside interconversion", Biochim. Biophys. Acta. (1997) Bol. 1335, No. 1-2, pp. 16-22.

Perchemlides, Peter et al., "Synthesis of α-L-idopyranosyl, (α-L-idopyranosyluronic acid), α-D-mannopyransoyl, and (α-D-mannopyranosyluronic acid) phosphates", Carbohydr. Res. (1967) vol. 3, No. 4, pp. 463-477.

* cited by examiner

SEQUENCE LISTING

<160> NUMBER OF SEQ ID NOS: 2

<210> SEQ ID NO 1
<211> LENGTH: 30

```
<212> TYPE: DNA
<213> ORGANISM: Artificial Sequence
<220> FEATURE:
<223> OTHER INFORMATION: primer

<400> SEQUENCE: 1
gtgaattcac aaaaaggata aaacaatggc                                    30

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
tcgaagcttg cgaaacacaa ttactcttt                                     29
```

PROCESS FOR SELECTIVELY PRODUCING 1-PHOSPHORYLATED SUGAR DERIVATIVE ANOMER AND PROCESS FOR PRODUCING NUCLEOSIDE

BACKGROUND OF THE INVENTION

1. Field of the Invention

This invention relates to a process for producing a 1-phosphorylated saccharide derivative. 1-phosphorylated saccharides are—widely distributed in the living world, are reaction substrates for a variety of enzymes and are utilized starting materials for preparing useful substances such as drugs and nutritional foods. Synthetic 1-phosphorylated saccharide derivatives have been expected to be used as starting materials for preparing drugs such as antiviral agents and enzyme inhibitors.

This invention also relates to a process for producing a nucleoside compound used as a starting material or drug substance for medical drugs such as antiviral, anticancer and antisense drugs.

2. Description of the Prior Art

There are known processes for producing a 1-phosphorylated saccharide such as:

1) condensation of a 1-bromosaccharide with a silver phosphate salt (J. Biol. Chem., Vol.121, p.465 (1937); J. Am. Chem. Soc., Vol.78, p.811 (1956); J. Am. Chem. Soc., Vol.79, p.5057 (1957));

2) condensation of a 1-halogenated saccharide with a triethylamine salt of dibenzylphosphoric acid (J. Am. Chem. Soc., Vol.77, p.3423 (1955); J. Am. Chem. Soc., Vol.80, p.1994 (1958); J. Am. Chem. Soc., Vol.106, p.7851 (1984); J. Org. Chem., Vol.59, p.690 (1994));

3) thermal condensation of a 1-acetylated saccharide with orthophosphoric acid (J. Org. Chem., Vol.27, p.1107 (1962); Carbohydrate Res., Vol.3, p.117 (1966); Carbohydrate Res., Vol.3, p.463 (1967); Can. J. Biochem., Vol.50, p.574 (1972));

4) condensation of dibenzylphoshoric acid with a saccharide activated at 1-position by imidation (Carbohydrate Res., Vol.61, p.181 (1978); Tetrahedron Lett., Vol.23, p.405 (1982));

5) treatment of a saccharide activated at 1-position by thallium or lithium alcolate with dibenzylphosphoric chloride (Carbohydrate Res., Vol.94, p.165 (1981); Chem. Lett., Vol.23, p.405 (1982));

6) phosphorolysis of a nucleoside utilizing action of nucleoside phosphorylase to form a 1-phoshorylated saccharide derivative (J. Biol. Chem., Vol.184, p.437 (1980)).

These processes have the following drawbacks.

A common problem in the chemical processes described in the above 1) to 5) is that it is difficult to establish a general synthetic method for preparing a desired isomer with a good selectivity due to variation in an anomer selectivity between α/β anomers owing to influence of a functional group adjacent to 1-position. For achieving selectivity and a good yield, the presence of 2-acetoxy or acetamino group is essential. However, since 2-deoxysaccharide is unstable, these synthetic processes may be limited to a considerably narrow application range. Thus, it is difficult to control anomer selectivity so that column chromatography purification is required, leading to a poor yield (Chem. Zvesti, Vol.28(1), p.115 (1974); Izv. Akad. Nauk SSSR, Ser. Khim., Vol.8, p.1843 (1975)).

Of course, there have been no reports for chemical preparation of a 1-phosphorylated 2-deoxyfuranose which is more unstable than a 1-phosphorylated 2-deoxypyranose, resulting in more difficult selectivity control.

In terms of 6), preparation of a nucleoside itself is difficult except a quite limited type of rebonucleosides such as inosine. A limited type of 1-phosphorylated saccharide derivatives such as ribose-1-phosphate can be, therefore, prepared. In addition, since a nucleoside itself as a starting material is expensive, the process is not satisfactory in its cost.

As described above, the term "nucleoside phosphorylase" is a generic name for enzymes capable of phosphorolysis of an N-glycoside bond in a nucleoside in the presence of phosphoric acid, which catalyze a reaction represented by the following equation:

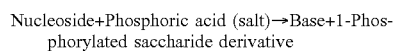
Nucleoside+Phosphoric acid (salt)→Base+1-Phosphorylated saccharide derivative The enzymes which may be generally categorized into two groups of purine nucleoside phosphorylases and pyrimidine nucleoside phosphorylases, are widely distributed in the living world; they are present in tissues of mammals, birds and fish; yeasts; and bacteria. The enzyme reaction is reversible and there have been disclosed methods for synthesis of a variety of nucleosides utilizing a reverse reaction; for syntheses of thymidine (thymine, adenine or guanine) (JP-A 01-104190), 2'-deoxyadenosine (JP-A 11-137290) or 2'-deoxyguanosine (JP-A 11-137290) from 2'-deoxyribose 1-phosphate and a nucleic-acid base.

Furthermore, Agric. Biol. Chem., Vol.50 (1), pp.121–126 (1986) has described a process where by a reaction using a purine nucleoside phosphorylase from Enterobacter aerogenes in the presence of phosphoric acid, inosine is decomposed into ribose 1-phosphate and hypoxanthine and the former isolated using an ion-exchange resin and 1,2,4-triazole-3-carboxamide are also treated with a purine nucleoside phosphorylase from Enterobacter aerogenes to prepare ribavirin as an antiviral agent.

However, as described above, an industrial process for producing a 1-phosphorylated saccharide derivative has not been established, and thus an industrial process for preparation of a universally useful nucleoside utilizing a reverse reaction of a nucleoside phosphorylase has been also not established.

Furthermore, since the reaction for forming a nucleoside from 1-phosphorylated saccharide derivative and a base utilizing the reverse reaction of the enzyme is reversible, there is a technical drawback that an inversion rate cannot be improved.

SUMMARY OF THE INVENTION

An objective of this invention is to provide a highly universal and anomer-selective process for preparing 1-phospholyrated saccharide derivative which is not influenced by difference in a saccharide skeleton such as furanose and pyranose, presence of a substituent such as a deoxysaccharide or a saccharide type, i.e., natural or synthetic.

Another objective of this invention is to provide a highly universal process for producing a nucleoside by treating a 1-phosphorylated saccharide derivative and a nucleic-acid base with a nucleoside phosphorylase and a method for improving an inversion rate for the nucleoside in the reaction.

In other words, the ultimate objective of this invention is to provide a process for producing a highly pure nucleoside with a lower cost by achieving the first and the second objectives above.

We have intensely made attempts for achieving the first objective. Finally, we have found that a 1-phosphorylated saccharide derivative is present in an equilibrium with an anomer and a dimer of the 1-pohsphorylated saccharide derivative under certain conditions and that the conditions may be adjusted to allow only a desired anomer to be precipitated as crystals so that the equilibrium may be displaced toward the preferable direction to provide the desired anomer with good selectivity and a high yield. Thus, based on the findings, we have achieved this invention.

Specifically, this invention encompasses the following embodiments.

(1) A process for selectively preparing either α or β isomer of a 1-phosphorylated saccharide derivative monomer comprising the steps of phosphorolyzing and isomerizing an anomer mixture of a 1-phosphorylated saccharide derivative to give α and β isomers of the 1-phosphorylated saccharide derivative monomer and selectively crystallizing one of these isomers to displace the equilibrium between these anomers.

(2) A process for selectively preparing either α or β isomer of a 1-phosphorylated saccharide derivative monomer comprising the steps of phosphorolyzing and isomerizing an anomer mixture of a 1-phosphorylated saccharide derivative represented by formula (I):

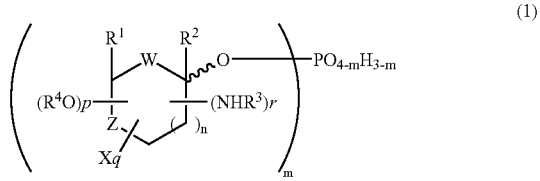

(1)

where $R^1$ and $R^2$ independently represents hydrogen, methyl, protected hydroxymethyl or protected carboxyl; $R^3$ represents acyl; $R^4$ represents a protective group for hydroxy; X represents halogen, alkoxy or alkylthio; W represents oxygen or sulfur; z represents oxygen, sulfur or optionally substituted carbon; m represents an integer of 1 to 3; n represents 0 or 1; p and q represents an integer of 0 to 4; and r represents 0 or 1; provided that p, q, r and n meet the conditions of $p+r \leq n+1$ and $q \leq 2 \times (n+1) - 2 \times (p+r)$ when Z is oxygen or sulfur and of $p+r \leq n+2$ and $q \leq 2 \times (n+2) - 2 \times (p+r)$ when Z is carbon, to give α and β isomers of the 1-phosphorylated saccharide derivative monomer and selectively crystallizing one of these isomers to displace the equilibrium between these anomers:

(3) A process for preparing a 1-phosphorylated saccharide derivative monomer represented by formula (3):

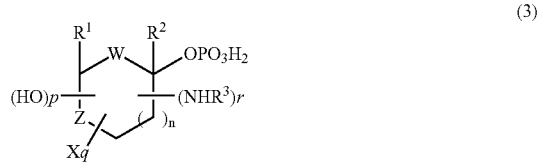

(3)

wherein $R^1$ and $R^2$ independently represents hydrogen, methyl, hydroxymethyl or carboxyl; $R^3$ represents hydrogen or acyl; and X, W, Z, n, p, q and r are as defined for formula (1), comprising the steps of phosphorolyzing and isomerizing an anomer mixture of a 1-phosphorylated saccharide derivative represented by formula (1) to give α and β isomers of the 1-phosphorylated saccharide derivative monomer; selectively crystallizing one of these isomers to displace the equilibrium between these anomers; and then removing the protective group represented by $R^4$.

(4) A trimer, dimer or monomer of a 1-phosphorylated saccharide derivative represented by formula (4):

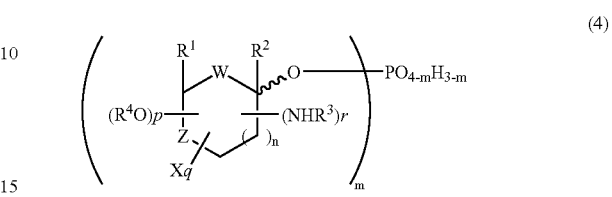

(4)

wherein $R^1$ and $R^2$ independently represents hydrogen, methyl, hydroxymethyl protected with substituted benzoyl or protected carboxyl; $R^4$ represents hydrogen or a protective group for hydroxy; and $R^3$, X, W, Z, m, n, p, q and r are as defined for formula (1), or salts thereof.

(5) A 1-phosphorylated saccharide derivative monomer represented by formula (5):

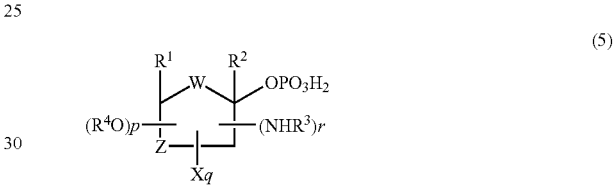

(5)

wherein p and q represents an integer of 0 to 3; r represents 0 or 1; and $R^1$, $R^2$, $R^3$, $R^4$, X, W and Z are as defined for formula (1); provided that p, q and r meet the conditions of $p+q+r \leq 3$ when Z is oxygen or sulfur and of $p+q+r \leq 5$ when Z is carbon, or salts thereof.

(6) A 1-phosphorylated saccharide derivative monomer represented by formula (6):

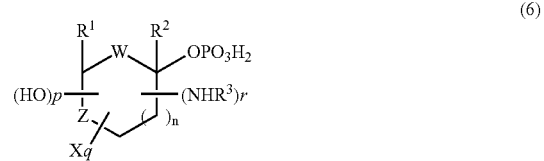

(6)

wherein $R^1$ and $R^2$ independently represents hydrogen, methyl, hydroxymethyl or carboxy; and $R^3$, X, W, Z, n, p, q and r are as defined for formula (1), or salts thereof.

(7) A 1-phosphorylated saccharide derivative monomer represented by formula (7):

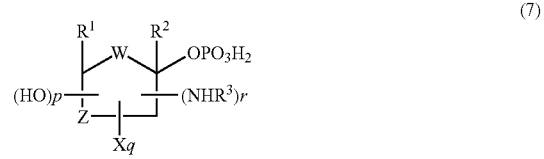

(7)

wherein p and q represents an integer of 0 to 3; r represents 0 or 1; and $R^1$, $R^2$, $R^3$, $R^4$, X, W and Z are defined for formula (1); provided that p, q and r meet the conditions of $p+r\leq 1$, $q\leq 2-2\times(p+r)$ when Z is oxygen or sulfur and of $p+r\leq 2$, $q\leq 4-2\times(p+r)$ when Z is carbon, or salts thereof.

(8) A process for preparing a 1-phosphorylated saccharide represented by formula (20):

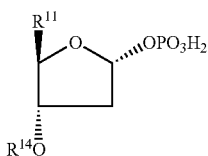
(20)

wherein $R^{11}$ represents protected hydroxymethyl and $R^{14}$ represents a protective group for hydroxy, comprising the steps of treating a compound represented by formula (18):

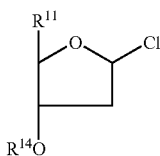
(18)

wherein $R^{31}$ and $R^{14}$ are as defined above, with phosphoric acid in the presence of a base to give an anomer mixture of a 1-phosphorylated saccharide derivative represented by formula (19):

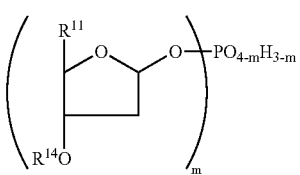
(19)

wherein $R^{11}$ and $R^{14}$ are as defined above and m is as defined in claim 2; phosphorolyzing and isomerizing the mixture; and displacing the equilibrium between the anomer isomers by selectively crystallizing an α-isomer formed.

(9) A process for preparing 2-deoxy-α-D-ribose-1-phosphate, comprising the steps of treating a compound represented by formula (18):

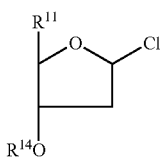
(18)

wherein $R^{11}$ represents protected hydroxymethyl and $R^{14}$ represents a protective group for hydroxy, with phosphoric acid in the presence of a base to give an anomer mixture of a 1-phosphorylated saccharide derivative represented by formula (19):

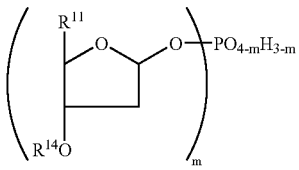
(19)

wherein $R^{11}$ and $R^{14}$ are as defined above and m is as defined in claim 2; phosphorolyzing and isomerizing the mixture; displacing the equilibrium between the anomer isomers by selectively crystallizing an α-isomer formed to give the α-isomer; and then removing the protective group.

We have intensely attempted for achieving the second objective and thus have established a highly universal process for preparing a nucleoside by utilizing a reverse reaction of nucleoside phosphorylases widely distributed in the living world in combination with the above preparation processes for a 1-phosphorylated saccharide derivative. We have further found that a metal cation capable of forming a water-insoluble salt with a phosphate ion may be present to allow a phosphate ion as a byproduct in the reaction to be precipitated as a water-insoluble salt, resulting in displacement of the reaction equilibrium toward the direction for nucleoside production and thus improvement in a reaction yield. Thus, we have achieved this invention providing a process for preparing a highly pure nucleoside with a lower cost.

This invention based on the above findings encompasses the following embodiments.

(10) A process for preparing a nucleoside represented by formula (8):

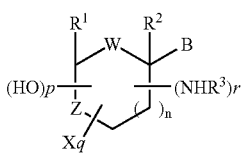
(8)

wherein B is a base independently selected from the group consisting of pyrimidine, purine, azapurine and deazapurine optionally substituted by halogen, alkyl, haloalkyl, alkenyl, haloalkenyl, alkynyl, amino, alkylamino, hydroxy, hydroxyamino, aminoxy, alkoxy, mercapto, alkylmercapto, aryl, aryloxy or cyano; and $R^1$, $R^2$, $R^3$, X, W, Z, n, p, q and r are as defined for formula (1), comprising the first procedure in the above (3) for preparing 1-phosphorylated saccharide derivative monomer comprising the steps of phosphorolyzing and isomerizing an anomer mixture of a 1-phosphorylated saccharide derivative to give α and β isomers of the 1-phosphorylated saccharide derivative monomer; selectively crystallizing one of these isomers to displace the equilibrium between these anomers; and then removing the protective group represented by $R^4$; and the second procedure of conducting an exchange reaction of the phosphate group in the 1-phosphorylated saccharide derivative obtained in the first procedure with a base by the action of a nucleoside phosphorylase.

(11) A process for preparing a nucleoside represented by formula (9):

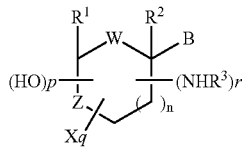
(9)

wherein B is as defined for formula (8); and $R^1$, $R^2$, $R^3$, $R^4$, X, W, Z, n, p, q and r are as defined for formula (1), comprising an exchange reaction of the phosphate group in the 1-phosphorylated saccharide derivative monomer in the above (6) with a base by the action of a nucleoside phosphorylase.

(12) A process for preparing a nucleoside represented by formula (10):

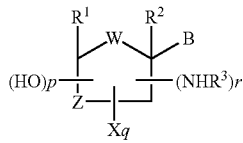
(10)

wherein B is as defined for formula (8); and $R^1$, $R^2$, $R^3$, $R^4$, X, W, Z, p, q and r are as defined for formula (1), comprising an exchange reaction of the phosphate group in the 1-phosphorylated saccharide derivative monomer in the above (7) with a base by the action of a nucleoside phosphorylase.

(13) A process for preparing a nucleoside represented by formula (21):

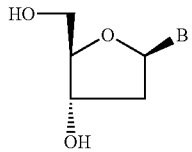
(21)

wherein B is as defined for formula (8) in claim 11, comprising the first procedure of preparing 2-deoxy-α-D-ribose-1-phosphate in the above (12) where $R^1$ is hydroxymethyl, $R^2$ is hydrogen, p and r are 0, and X is fluorine; and the second procedure of conducting an exchange reaction of the phosphate group in the 1-phosphorylated saccharide derivative obtained in the first procedure with a base by the action of a nucleoside phosphorylase.

In the embodiments of the above (10) to (13), a nucleoside phosphorylase may be at least one selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

A nucleoside phosphorylase activity may be obtained using a microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

In the embodiments of the above (10) to (13), a metal cation capable of forming a water-insoluble salt with a phosphate ion may be present in the reaction solution during the exchange reaction of a phosphate group in the 1-phosphorylated saccharide derivative monomer with a base by the action of a nucleoside phosphorylase.

The metal cation capable of forming a water-insoluble salt with the phosphate ion in the embodiments of the above (10) to (13) may be at least one metal cation selected from the group consisting of calcium, barium, aluminum and magnesium ions.

Furthermore, this invention encompasses a compound represented by any of formulas (11) to (13) and (20).

That is, this invention also encompasses:

a synthetic nucleoside, which is not naturally produced represented by formula (11):

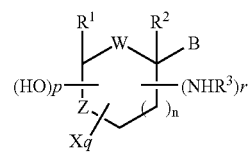
(11)

wherein B, $R^1$, $R^2$, $R^3$, $R^4$, X, W, Z, n, p, q and r are as defined for formulas (1) and (8) or its salt, excluding trifluorothymidine, ribavirin, orotidine, uracil arabinoside, adenine arabinoside, 2-methyl-adenine arabinoside, 2-chloro-hypoxanthine arabinoside, thioguanine arabinoside, 2,6-diaminopurine arabinoside, cytosine arabinoside, guanine arabinoside, thymine arabinoside, enocitabine, gemcitabine, azidothymidine, idoxuridine, dideoxyadenosine, dideoxyinosine, dideoxycytidine, didehydrodeoxythymidine, thiadideoxycytidine, sorivudine, 5-methyluridine, virazole, thioinosine, tegafur, doxifluridine, bredinin, nebularine, allopurinol uracil, 5-fluorouracil, 2'-aminouridine, 2'-aminoadenosine, 2'-aminoguanidine, 2-chloro-2'-aminoinosine, DMDC and FMDC;

a synthetic nucleoside, which is not naturally produced represented by formula (12):

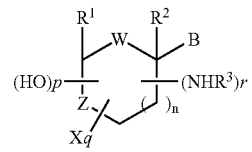
(12)

wherein B, $R^1$, $R^2$, $R^3$, $R^4$, X, W, Z, n, p, q and r are as defined for formulas (1) and (8) or its salt, excluding trifluorothymidine, ribavirin, orotidine, uracil arabinoside, adenine arabinoside, 2-methyl-adenine arabinoside, 2-chloro-hypoxanthine arabinoside, thioguanine arabinoside, 2,6-diaminopurine arabinoside, cytosine arabinoside, guanine arabinoside, thymine arabinoside, enocitabine, gemcitabine, azidothymidine, idoxuridine, dideoxyadenosine, dideoxyinosine, dideoxycytidine, didehydrodeoxythymidine, thiadideoxycytidine, sorivudine, 5-methyluridine, virazole, thioinosine, tegafur, doxifluridine, bredinin, nebularine, allopurinol uracil, 5-fluorouracil, 2'-aminouridine, 2'-aminoadenosine, 2'-aminoguanidine, 2-chloro-2'-aminoinosine, DMDC and FMDC;

a nucleoside represented by formula (13):

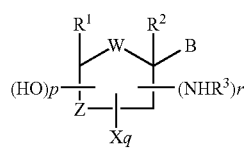

(13)

wherein B, $R^1$, $R^2$, $R^3$, $R^4$, X, W, Z, n, p, q and r are as defined for formulas (1) and (8) or its salt, excluding trifluorothymidine, ribavirin, orotidine, uracil arabinoside, adenine arabinoside, 2-methyl-adenine arabinoside, 2-chloro-hypoxanthine arabinoside, thioguanine arabinoside, 2,6-diaminopurine arabinoside, cytosine arabinoside, guanine arabinoside, thymine arabinoside, enocitabine, gemcitabine, azidothymidine, idoxuridine, dideoxyadenosine, dideoxyinosine, dideoxycytidine, didehydrodeoxythymidine, thiadideoxycytidine, sorivudine, 5-methyluridine, virazole, thioinosine, tegafur, doxifluridine, bredinin, nebularine, allopurinol uracil, 5-fluorouracil, 2'-aminouridine, 2'-aminoadenosine, 2'-aminoguanidine, 2-chloro-2'-aminoinosine, DMDC and FMDC; and a 1-phosphorylated saccharide represented by formula (20):

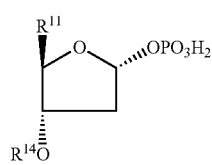

(20)

wherein $R^{11}$ and $R^{14}$ are as defined for formula (18), or its salt.

DETAILED DESCRIPTION OF PREFERRED EMBODIMENTS

This invention will be described in detail.

Saccharides which may used in this invention include, but not limited to, residues derived from D- and L-type natural monosaccharides including 6-deoxysaccharides such as fucose, rhamnose, digitoxose, oleandrose and quinovose, hexoses such as allose, altrose, glucose, mannose, gulose, idose, galactose and talose, pentoses such as ribose, arabinose, xylose and lyxose, tetroses such as erythrose and threose, aminosaccharides such as glucosamine and daunosamine, uronic acids such as glucuronic acid and galacturonic acid, ketoses such as psicose, fructose, sorbose, tagatose and pentulose, and deoxysaccharides such as 2-deoxyribose; residues derived from synthetic pyranose and furanose saccharides; and saccharide residue derivatives in which hydroxy and/or amino groups in any of the above residues are protected or acylated or saccharides having a halogenated saccharide residue in which hydroxy is replaced with halogen such as fluorine.

In this invention, a 1-phosphorylated saccharide derivative refers to a saccharide derivative in which among residues derived from natural or synthetic monosaccharide, 1-hydroxy is phosphorylated. Unless otherwise indicated, it may include a monomer, dimer or trimer or a mixture thereof, where there are no restrictions to its mixture ratio.

A protective group in terms of "protected hydroxymethyl" and "a protective group of hydroxy" means that which may be removed by an appropriate chemical process such as hydrogenolysis, hydrolysis and photolysis, including formyl, acyl, silyl, alkyl, aralkyl, carbonyl, preferably formyl, aliphatic acyl, aromatic acyl, silyl, alkoxyalkyl, halogenated alkyl, aralkyl, alkoxycarbonyl and aralkyloxycarbonyl.

Aliphatic acyl may be alkylcarbonyl and halogenated lower alkylcarbonyl.

Examples of alkylcarbonyl include acetyl, propionyl, butyryl, isobutyryl, pentanoyl, pivaloyl, valeryl, isovaleryl, octanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl and octadecylcarbonyl.

Examples of halogenated lower alkylcarbonyl include chloroacetyl, dichloroacetyl, trichloroacetyl and trifluoroacetyl.

Aromatic acyl may be arylcarbonyl, halogenated arylcarbonyl, lower-alkylated arylcarbonyl, lower-alkoxylated arylcarbonyl, nitrated arylcarbonyl, lower-alkoxycarbonylated arylcarbonyl or arylated arylcarbonyl.

Examples of arylcarbonyl include benzoyl, α-naphthoyl and β-naphthoyl.

Examples of halogenated arylcarbonyl include 2-fluorobenzoyl, 3-fluorobenzoyl, 4-fluorobenzoyl, 2-chlorobenzoyl, 3-chlorobenzoyl, 4-chlorobenzoyl, 2-bromobenzoyl, 3-bromobenzoyl, 4-bromobenzoyl, 2,4-dichlorobenzoyl, 2,6-dichlorobenzoyl, 3,4-dichlorobenzoyl and 3,5-dichlorobenzoyl.

Examples of lower-alkylated arylcarbonyl include 2-toluoyl, 3-toluoyl, 4-toluoyl and 2,4,6-trimethylbenzoyl.

Examples of lower-alkoxy arylcarbonyl include 2-anisoyl, 3-anisoyl and 4-anisoyl.

Examples of nitrated arylcarbonyl include 2-nitrobenzoyl, 3-nitrobenzoyl, 4-nitrobenzoyl and 3,5-dinitrobenzoyl.

Examples of lower-alkoxycarbonylated arylcarbonyl include 2-(methoxycarbonyl)benzoyl. Examples of arylated arylcarbonyl include 4-phenylbenzoyl.

Silyl may be lower-alkylsilyl and aryl-substituted lower-alkylsilyl.

Examples of lower-alkyl silyl include trimethylsilyl, triethylsilyl, isopropyldimethylsilyl, tert-butyldimethylsilyl, methyldiisopropylsilyl and triisopropylsilyl.

Examples of aryl-substituted lower-alkylsilyl include diphenylmethylsilyl, diphenylisopropylsilyl and phenyldiisopropylsilyl.

Aralkyl may be benzyl, aralkyl substituted with lower alkyl, aralkyl substituted with lower alkoxy, aralkyl substituted with nitro, aralkyl substituted with halogen or aralkyl substituted with cyano.

Examples of these include 2-methylbenzyl, 3-methylbenzyl, 4-methylbenzyl, 2,4,6-trimethylbenzyl, 2-methoxybenzyl, 3-methoxybenzyl, 4-methoxybenzyl, 2-nitrobenzyl, 3-nitrobenzyl, 4-nitrobenzyl, 2-chlorobenzyl, 3-chlorobenzyl, 4-chlorobenzyl, 2-bromobenzyl, 3-bromobenzyl, 4-bromobenzyl, 2-cyanobenzyl, 3-cyanobenzyl and 4-cyanobenzyl.

Aralkyloxycarbonyl may be aralkyloxycarbonyl substituted with lower alkyl, aralkyloxycarbonyl substituted with lower alkoxy, aralkyloxycarbonyl substituted with nitro, aralkyloxycarbonyl substituted with halogen or aralkyloxycarbonyl substituted with cyano.

Examples of these include 2-methylbenzyloxycarbonyl, 3-methylbenzyloxycarbonyl, 4-methylbenzyloxycarbonyl, 2,4,6-trimethylbenzyloxycarbonyl, 2-methoxybenzyloxycarbonyl, 3-methoxybenzyloxycarbonyl, 4-methoxybenzyloxycarbonyl, 2-nitrobenzyloxycarbonyl, 3-nitrobenzyloxycarbonyl, 4-nitrobenzyloxycarbonyl, 2-chlorobenzyloxycarbonyl, 3-chlorobenzyloxycarbonyl, 4-chlorobenzyloxycarbonyl, 2-bromobenzyloxycarbonyl, 3-bromobenzyloxycarbonyl, 4-bromobenzyloxycarbonyl, 2-cyanobenzyloxycarbonyl, 3-cyanobenzyloxycarbonyl and 4-cyanobenzyloxycarbonyl.

Alkoxycarbonyl may be lower-alkoxycarbonyl, alkoxycarbonyl substituted with halogen or alkoxycarbonyl substituted with alkylsilyl.

Examples of lower-alkoxycarbonyl include methoxycarbonyl, ethoxycarbonyl, propoxycarbonyl, butoxycarbonyl, sec-butoxycarbonyl and tert-butoxycarbonyl.

Examples of alkoxycarbonyl substituted with halogen include 2,2,2-trichloroethoxycarbonyl. Examples of alkoxycarbonyl substituted with alkylsilyl include 2-trimethylsilylethoxycarbonyl.

Alkyl may be alkoxyalkyl such as methoxyethyl, ethoxymethyl, 2-methoxyethyl and 2-methoxyethoxymethyl; halogenated alkyl such as 2,2,2-trichloroethyl; or lower alkyl substituted with aryl such as benzyl, α-naphthylmethyl, β-naphthylmethyl, diphenylmethyl and triphenylmethyl.

Among these, aliphatic acyl, aromatic acyl and aralkyl are preferable; 4-toluoyl, 4-chlorobenzoyl and benzyl are more preferable. A protective group in terms of "protected carboxyl" in $R^1$ and $R^2$ refers to that which may be removed by an appropriate chemical process such as hydrogenolysis, hydrolysis and photolysis, including preferably lower alkyl such as methyl, ethyl, n-propyl, isopropyl, n-butyl, isobutyl, sec-butyl and tert-butyl; silylated lower alkyl such as 2-(trimethylsilyl)ethyl and 2-(triethylsilyl)ethyl; or the above aralkyl or alkoxyalkyl, more preferably methyl, tert-butyl or benzyl.

Halogen in terms of X refers to fluorine, chlorine, bromine or iodine.

Alkoxy and alkylthio in terms of X may be alkoxy and alkylthio having the above lower alkyl, aralkyl or alkoxyalkyl, preferably methoxy, methoxyethoxy or methylthio.

Optionally substituted carbon in terms of Z refers to carbon having one or two of the substituent represented by the formula (Xq and $NHR^3$) or when having no substituents, carbon having hydrogen atoms.

Acyl in terms of $R^3$ may be the above aliphatic acyl, aromatic acyl, alkoxycarbonyl or aralkyloxycarbonyl, or lower-alkanesulfonyl such as methanesulfonyl and trifluoromethanesulfonyl or arylsulfonyl such as benzenesulfonyl and p-toluenesulfonyl; preferably, aliphatic acyl, aromatic acyl or lower-alkanesulfonyl; specifically, acetyl, trifluoroacetyl, benzoyl and methanesulfonyl. When more than one of $NHR^3$ are used as a substituent, $R^3$s in individual $NHR^3$ independently represent any of the above radicals.

A protective group in "protected hydroxymethyl" and "a protective group for hydroxy" in terms of $R^4$, $R^{11}$ and $R^{14}$ may be selected from those described for $R^1$ and $R^2$.

Saccharide residues having a structure represented by any of formulas (1) to (17) may be preferably, but not limited to, those derived from a natural monosaccharide described above, those derived from a synthetic saccharide, derivatives from the saccharide residues or halogenated saccharide residues, as described above.

Salts of a compound represented by any of formulas (4) to (7) may be those formed by a phosphate radical in the compound. Examples of such a salt include alkali metal salt such as sodium, potassium and lithium salts; alkaline earth metal salt such as magnesium, calcium and barium salts; metal salt such as aluminum and iron salts; ammonium salt; or alkylamine salt such as primary, secondary and tertiary alkyl amine salts.

Primary amine herein may be alkylamine such as methylamine, ethylamine, propylamine, isopropylamine, butylamine, hexylamine and octylamine; cycloalkylamine such as cyclohexylamine; or benzylamine.

Secondary amine may be dialkylamine such as diethylamine, diisopropylamine, dibutylamine, dihexylamine and dioctylamine; dicycloalkylamine such as dicyclohexylamine; or cyclic amine such as piperidine, morpholine and N-methylpiperadine.

Tertiary amine may be tertiary-alkylamine such as trimethylamine, triethylamine, tripropylamine, N-ethyldiisopropylamine, tributylamine, trihexylamine, trioctylamine, N-ethyldicyclohexylamine, N-methylpiperidine, N-methylmorpholine and N,N,N',N'-tetramethylethylenediamine; aniline compound such as aniline, N,N-dimethylaniline, N,N-diethylaniline, N,N-dibutylaniline and N,N-dioctylaniline; pyridine compound such as pyridine, 2,6-dimethylpyridine, 2,4,6-lutidine and nicotinamide; amino acid such as glycine, alanine, proline, lysine, arginine and glutamine; or optically active amine such as cinchonidine, 1-(1-naphthyl)ethylamine and 1-phenylethylamine, all of which include monovalent and bivalent salts.

A compound represented by any of formula (4) to (7) of this invention may absorb moisture to have adsorbed water or become a hydrate, all of which may be encompassed by this invention.

An anomer mixture of a 1-phosphorylated saccharide derivative according to this invention may be prepared by, but not limited to, a reaction represented by reaction formula (I):

Reaction Formula (I)

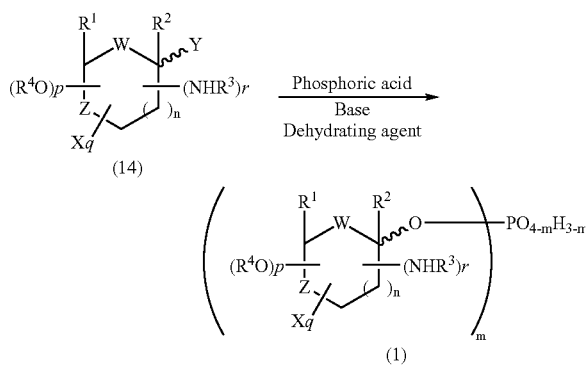

In this formula, $R^1$, $R^2$, $R^3$, $R^4$, X, W, Z, m, n, p, q and r are as defined for formula (1), and Y represents fluorine, chlorine, bromine or iodine. When m is 1, 2 or 3, phosphoric acid tri-, di- or mono-ester is provided, respectively. These are referred to as 1-phosphorylated saccharide derivative trimer, 1-phosphorylated saccharide derivative dimer and 1-phosphorylated saccharide derivative monomer, respectively. Furthermore, 1-phosphorylated saccharide derivative trimer, 1-phosphorylated saccharide derivative dimer and 1-phosphorylated saccharide derivative monomer are collectively referred to as a 1-phosphorylated saccharide derivative, for which there are no restrictions to its mixture ratio.

A preferable phosphoric acid may be, but not limited to, one with a lower water content such as orthophosphoric acid.

There are no restrictions to a base as long as it does not inhibit the reaction and functions as a deoxidizer. Preferable inorganic bases include carbonates and hydroxides of alkali and alkaline earth metals. Preferable organic bases include tertiary alkylamines, anilines, pyridines and optically active amines.

A dehydrating agent may be used when moisture from a solvent or an additive adversely affects the reaction. There are no restrictions to a dehydrating agent as long as it has adequate adsorptivity or reactivity with water; preferably molecular sieves and phosphorus pentoxide.

The reaction is generally conducted in the presence of a solvent. There are no restrictions to a solvent as long as it does not inhibit the reaction and dissolve starting materials to some degree. Solvents which may be used include aliphatic hydrocarbons such as hexane and heptane; aromatic hydrocarbons such as benzene, toluene, xylene and anisole; halogenated hydrocarbons such as methylene chloride, chloroform, carbon tetrachloride, dichloroethane, chlorobenzene and dichlorobenzene; esters such as ethyl formate, ethyl acetate, propyl acetate, n-butyl acetate and diethyl carbonate; ethers such as diethyl ether, diisopropyl ether, tetrahydrofuran, dioxane, dimethoxyethane and diglyme; nitriles such as acetonitrile, propionitrile and isobutylnitrile; amides such as formamide, N,N-dimethylformamide, N,N-dimethylacetamide, N-methyl-2-pyrrolidone, N-methylpyrrolidinone and N,N-dimethyl-2-imidazolydinone; ketones such as acetone, 2-butanone, methyl isopropyl ketone and methyl isobutyl ketone; and a mixture of two or more selected therefrom.

There are no restrictions to a reaction temperature; generally −80° C. to 60° C., preferably −10° C. to 25° C.

A reaction period may vary depending on many factors such as starting materials, reagents, the type of a solvent and a reaction temperature; generally 1 min to 24 hours, preferably 10 min to 2 hours for completing the reaction.

There are no restrictions. to a ratio of a saccharide derivative (14) to phosphoric acid; the reaction is generally conducted with a ratio of compound (14): phosphoric acid=1:10 to 3:1. In this case, the product (1) may be a mixture of the compounds whose saccharide residue number (i.e., m) coupled with phosphoric acid is 1, 2 or 3, depending on the ratio of compound (14): phosphoric acid.

Furthermore, a 1-phosphorylated saccharide derivative (16a) or (16b) with either α- or β-form may be prepared by a reaction represented by reaction formula (II):

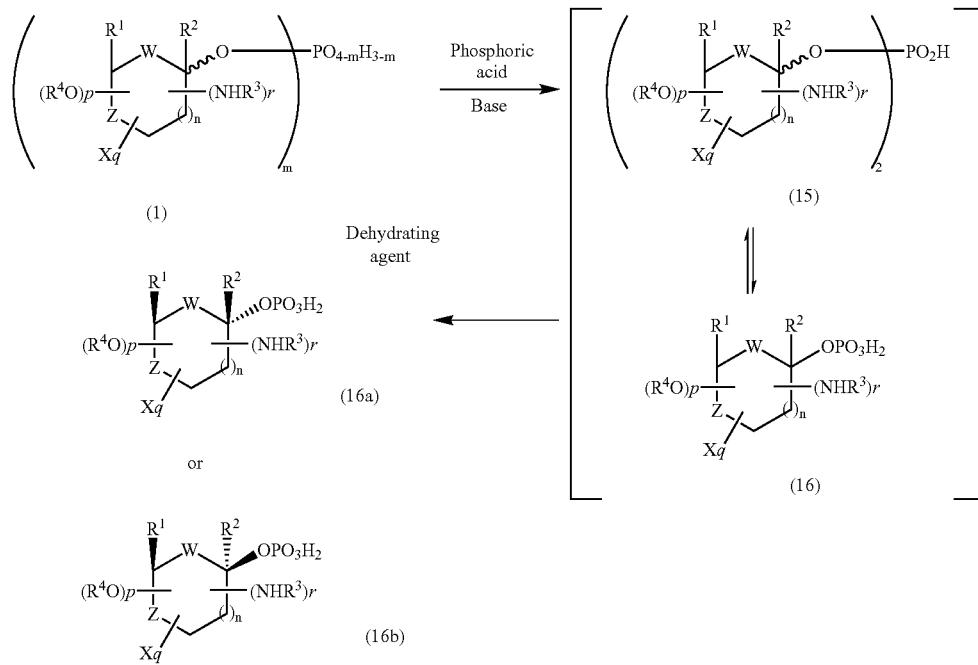

In this formula, $R^1$, $R^2$, $R^3$, $R^4$, X, W, Z, m, n, p, q and r are as defined for formula (1).

According to this preparation process, the 1-phosphorylated saccharide derivative represented by formula (15) may be a monomer, dimer or trimer or a mixture thereof in any mixture ratio because they may be converted into the 1-phosphorylated saccharide derivative represented by formula (16) in the reaction system.

A preferable phosphoric acid may be, but not limited to, one with a lower water content such as orthophosphoric acid.

A base is important for forming a salt with the phosphate group in compound (16) to selectively crystallize one of α- and β-compounds, (16a) or (16b). The most suitable base may be selected in the light of a solvent used in the reaction;

preferably, the above inorganic bases, tertiary alkylamines, anilines, pyridines, amino acids and optically active amines, and salts formed include monovalent and bivalent salts.

A dehydrating agent may be used when moisture from a solvent or an additive adversely affects the reaction. There are no restrictions to a dehydrating agent as long as it has adequate adsorptivity or reactivity with water; preferably molecular sieves and phosphorus pentoxide.

The reaction is generally conducted in the presence of a solvent. There are no restrictions to a solvent as long as it does not inhibit the reaction, dissolve starting materials to some degree and promotes selective crystallization of one of the α- and β-forms, (16a) or (16b), generated by salt formation of the phosphate group in compound (16), including the above aliphatic hydrocarbons, aromatic hydrocarbons, halogenated hydrocarbons, esters, ethers, nitrites, amides, ketones and a mixture of two or more selected therefrom.

There are no restrictions to a reaction temperature as long as it accelerates the equilibrium reaction between compounds (15) and (16) for promoting selective crystallization of one of the α- and β-forms, (16a) or (16b), generated by salt formation of the phosphate group in compound (16); generally −80° C. to 60° C., preferably −10° C. to 25° C.

A reaction period may vary depending on many factors such as starting materials, reagents, the type of a solvent and a reaction temperature; generally 3 hours to 1 week, preferably 6 hours to 24 hours for completing the reaction.

There are no restrictions to a ratio of a saccharide derivative (1) to phosphoric acid; the reaction is generally conducted with a ratio of compound (1): phosphoric acid=1:10 to 3:1, where the pH of the reaction system is generally 1 to 7, suitably in an acidic range from 1 to 4.

The 1-phosphorylated saccharide derivative (16a) or (16b) with either α- or β-form may be isolated as a phosphate with a base other than that used in the reaction system by a salt-exchange reaction.

Bases which may be herein used include the above inorganic bases, primary alkylamines, secondary alkylamines, tertiary alkylamines, anilines, pyridines, amino acids and optically active amines, and salts formed include monovalent and bivalent salts.

The protective group may be removed by reaction formula (III) to prepare a 1-phosphorylated saccharide derivative (17a) or (17b).

Reaction Formula (III)

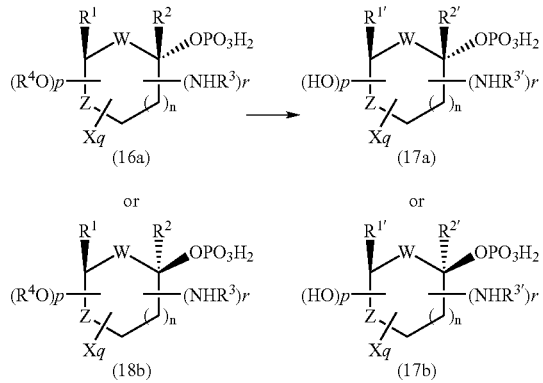

In this formula, $R^1$, $R^2$, $R^3$, $R^4$, X, W, Z, n, p, q and r are as defined for formula (1); $R^{1'}$ and $R^{2'}$ independently represent hydrogen, methyl, hydroxymethyl or carboxyl; and $R^{3'}$ represents hydrogen or acyl.

When using the above aliphatic acyl, aromatic acyl or alkoxy carbonyl as a protective group for hydroxymethyl in $R^1$ and $R^2$ or hydroxy in $R^4$, or using the above lower alkyl as a protective group for carboxyl in $R^1$ and $R^2$ in compound (16a) or (16b), it may be removed by treating the compound with a base in an aqueous solvent. Bases which may be used include preferably alkali metal carbonates such as sodium carbonate and potassium carbonate; alkali metal hydroxides such as lithium hydroxide, sodium hydroxide and potassium hydroxide; ammonium hydroxides such as ammonium hydroxide and tetra-n-butylammonium hydroxide; and the above inorganic bases, primary alkylamines, secondary alkylamines and tertiary alkylamines.

Solvents which may be used include, with no restrictions, those used in a common hydrolysis; preferably water; alcohols such as methanol, ethanol, n-propanol and isopropanol; and the above ethers. A reaction temperature and a reaction period vary, with no restrictions, depending on many factors such as starting materials and a base used; generally the reaction may be completed at −10° C. to 100° C. for 1 hour to 5 days. The protective group $R^3$ may be left or simultaneously removed as appropriate by adjusting a reaction temperature, a reaction period and the equivalent values of reagents.

When using the above aralkyl or aralkyloxycarbonyl as a protective group for hydroxymethyl in $R^1$ and $R^2$ or hydroxy in $R^4$ or using the above aralkyl as a protective group for carboxy in $R^1$ and $R^2$ in compound (16a) or (16b), they may be removed by, for example, catalytic hydrogenation using a metal catalyst.

The catalyst may be preferably selected from palladium-carbon, Raney nickel, platinum oxide, platinum black, rhodium-aluminum oxide, triphenylphosphine-rhodium chloride and palladium-barium sulfate. There are no restrictions to a reaction pressure. Generally, a solvent used may be any of those used in a common hydrolysis with no restrictions. It may be preferably selected from water; alcohols such as methanol, ethanol, n-propanol and isopropanol; the above ethers; and the above esters. A reaction temperature and a reaction period vary, with no restrictions, depending on many factors such as starting materials and a base used; generally the reaction may be completed at −10° C. to 100° C. for 1 hour to 5 days. The protective group $R^3$ may be generally left.

When using the above silyl as a protective group for hydroxymethyl in $R^1$ and $R^2$ or hydroxy in $R^4$ or using the above silylated lower alkyl as a protective group for carboxy in $R^1$ and $R^2$ in compound (16a) or (16b), they may be removed by, for example, using a compound which can generate fluoride anion such as tetra-n-butylammonium fluoride.

There are no restrictions to a solvent as long as it does not inhibit the reaction; for example, the above ethers may be used. A reaction temperature and a reaction period vary, with no restrictions, depending on many factors such as starting materials and a base used; generally the reaction may be completed at −10° C. to 50° C. for 10 min to 10 hours. The protective group $R^3$ may be generally left.

In removing any protective group, a phosphate group in a product is obtained as a salt with a base present in a reaction system. The salt may be, if necessary, converted into a salt with another base. In such a case, a base used may be selected from the above inorganic bases, primary alkylamines, secondary alkylamines, tertiary alkylamines, anilines, pyridines, amino acids and optically active amines, and salts formed include monovalent and bivalent salts.

A 1-phosphorylated saccharide derivative as used herein is a saccharide or its derivative in which a phosphoric acid moiety is coupled at 1-position via an ester linkage.

It may be specifically represented by formula (6):

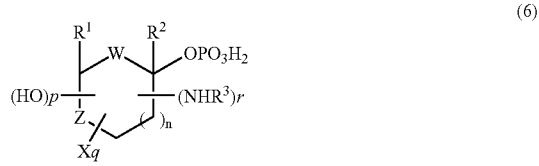

wherein $R^1$ and $R^2$ independently represent hydrogen, methyl, hydroxymethyl or carboxy; $R^3$, X, W, Z, n, p, q and r are as defined for formula (4).

Typical examples include, but not limited to, ribose-1-phosphate, 2-deoxyribose-1-phosphate, 2,3-dideoxyribose-1-phosphate and arabinose-1-phosphate, but any derivative may be used without distinction as long as it can be obtained by any of the above highly universal and anomer-selective preparation processes.

Examples of a saccharide derived from a natural product which constitutes a 1-phosphorylated saccharide derivative include, but not limited to, aldopentoses such as D-arabinose, L-arabinose, D-xylose, L-lyxose and D-ribose; ketopentoses such as D-xylose, L-xylose and D-ribulose; aldohexoses such as D-galactose, L-galactose, D-glucose, D-talose and D-mannose; ketohexoses such as D-tagatose, L-sorbose, D-psicose and D-fructose; deoxysaccharides such as D-2-deoxyribose, D-2,3-dideoxyribose, D-fucose, L-fucose, D-rhamnose, L-rhamnose, D-fucopyranose, L-fucopyranose, D-rhamnofuranose, L-rhamnofuranose, D-allomethylose, D-quinovose, D-antiallose, D-talomethylose, L-talomethylose, D-digitalose, D-digitoxose, D-cymarose, tyvelose, abequose, paratose, colitose and ascarilose; aminosaccharides such as glucosamine and daunosamine; and uronic acids such as glucuronic acid and galacturonic acid.

There will be described a process for preparing a nucleoside according to this invention. A base used in this process is a natural or synthetic base selected from pyrimidine, purine, azapurine and deazapurine, which may be substituted with halogen, alkyl, haloalkyl, alkenyl, haloalkenyl, alkynyl, amino, alkylamino, hydroxy, hydroxyamino, aminoxy, alkoxy, mercapto, alkylmercapto, aryl, aryloxy and/or cyano.

Examples of halogen as a substituent include chlorine, fluorine, bromine and iodine. Examples of alkyl include lower alkyls with 1 to 7 carbon atoms such as methyl, ethyl and propyl. Examples of haloalkyl include those having an alkyl with 1 to 7 carbon atoms such as fluoromethyl, difluoromethyl, trifluoromethyl, bromomethyl and bromoethyl. Examples of alkenyl include those with 2 to 7 carbon atoms such as vinyl and allyl. Examples of haloalkyl include those having alkenyl with 2 to 7 carbon atoms such as bromovinyl and chlorovinyl. Examples of alkynyl include those with 2 to 7 carbon atoms such as ethynyl and propynyl. Examples of alkylamino include those having alkyl with 1 to 7 carbon atoms such as methylamino and ethylamino. Examples of alkoxy include those with 1 to 7 carbon atoms such as methoxy and ethoxy. Examples of alkylmercapto include those having alkyl with 1 to 7 carbon atoms such as methylmercapto and ethylmercapto. Examples of aryl include phenyl; alkylphenyls having alkyl with 1 to 5 carbon atoms such as methylphenyl and ethylphenyl; alkoxyphenyls having alkoxy with 1 to 5 carbon atoms such as methoxyphenyl and ethoxyphenyl; alkylaminophenyls having alkylamino with 1 to 5 carbon atoms such as dimethylaminophenyl and diethylaminophenyl; and halogenophenyls such as chlorophenyl and bromophenyl.

Examples of a pyrimidine base include cytosine, uracil, 5-fluorocytosine, 5-fluoro uracil, 5-chlorocytosine, 5-chlorouracil, 5-bromocytosine, 5-bromouracil, 5-iodocytosine, 5-iodouracil, 5-methylcytosine, 5-methyluracil (thymine), 5-ethylcytosine, 5-ethyluracil, 5-fluoromethylcytosine, 5-fluoromethyluracil, 5-trifluorocytosine, 5-trifluorouracil, 5-vinyluracil, 5-bromovinyluracil, 5-chlorovinyluracil, 5-ethynylcytosine, 5-ethynyluracil, 5-propynyluracil, pyrimidin-2-one, 4-hydroxyaminopyrimidin-2-one, 4-aminoxypyrimidin-2-one, 4-methoxypyrimidin-2-one, 4-acetoxypyrimidin-2-one, 4-fluoropyrimidin-2-one and 5-fluoropyrimidin-2-one.

Examples of a purine base include purine, 6-aminopurine (adenine), 6-hydroxypurine, 6-fluoropurine, 6-chloropurine, 6-methylaminopurine, 6-dimethylaminopurine, 6-trifluoromethylaminopurine, 6-benzoylaminopurine, 6-acetylaminopurine, 6-hydroxyaminopurine, 6-aminoxypurine, 6-methoxypurine, 6-acetoxypurine, 6-benzoyloxypurine, 6-methylpurine, 6-ethylpurine, 6-trifluoromethylpurine, 6-phenylpurine, 6-mercaptopurine, 6-methylmercaptopurine, 6-aminopurine-1-oxide, 6-hydroxypurine-1-oxide, 2-amino-6-hydroxypurine (guanine), 2,6-diaminopurine, 2-amino-6-chloropurine, 2-amino-6-iodopurine, 2-aminopurine, 2-amino-6-mercaptopurine, 2-amino-6-methylmercaptopurine, 2-amino-6-hydroxyaminopurine, 2-amino-6-methoxypurine, 2-amino-6-benzoyloxypurine, 2-amino-6-acetoxypurine, 2-amino-6-methylpurine, 2-amino-6-cyclopropylaminomethylpurine, 2-amino-6-phenylpurine, 2-amino-8-bromopurine, 6-cyanopurine, 6-amino-2-chloropurine (2-chloroadenine) and 6-amino-2-fluoropurine (2-fluoroadenine).

Examples of an azapurine and a deazapurine bases include 6-amino-3-deazapurine, 6-amino-8-azapurine, 2-amino-6-hydroxy-8-azapurine, 6-amino-7-deazapurine, 6-amino-1-deazapurine and 6-amino-2-azapurine.

A nucleoside phosphorylase is a generic name for enzymes capable of phosphorolysis of an N-glycoside bond in a nucleoside in the presence of phosphoric acid and this invention utilizes its reverse reaction. An enzyme used in the reaction may be of any type or origin as long as it has an activity of forming a desired nucleoside from a corresponding 1-phosphorylated saccharide derivative and a base. The enzymes may be generally categorized into two types, purine and pyrimidine types. Examples of a purine type enzyme include purine nucleoside phosphorylase (EC2.4.2.1) and guanosine nucleoside phosphorylase (EC2.4.2.15). Examples of a pyrimidine type enzyme include pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

A microorganism expressing a nucleoside phosphorylase in this invention may be, with no restrictions, any microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

Preferable examples of such a microorganism include strains belonging to *Nocardia, Microbacterium, Corynebacterium, Brevibacterium, Cellulomonas, Flabobacterium, Kluyvere, Micobacterium, Haemophilus, Micoplana, Protaminobacter, Candida, Saccharomyces, Bacillus, thermophile Bacillus, Pseudomonas, Micrococcus, Hafnia, Proteus, Vibrio, Staphyrococcus, Propionibacterium, Sartina, Planococcus, Escherichia, Kurthia, Rhodococcus, Acinetobacter, Xanthobacter, Streptomyces, Rhizobium, Salmonella, Klebsiella, Enterobacter, Erwinia, Aeromonas, Citrobacter, Achromobacter, Agrobacterium, Arthrobacter* and *Pseudonocardia.*

Recent advance in molecular biology and genetic engineering has allowed us to analyze molecular-biological properties, an amino acid sequence and so on of a nucleoside phosphorylase in the above strain for obtaining the gene for the protein from the strain, to constitute a recombinant plasmid in which a control region required for the gene and its expression is inserted, to introduce the plasmid into a given host and to produce a gene recombinant strain expressing the protein, and these processes have become relatively easier. In the light of the recent technical level, such a gene recombinant strain in which a gene for a nucleoside phosphorylase is introduced in a given host shall be also included in a microorganism expressing a nucleoside phosphorylase according to this invention.

A control region required for expression herein may be a promoter sequence (including an operator sequence controlling transcription), a ribosome binding sequence (SD sequence), a transcription termination sequence, or the like. Examples of a promoter sequence include a trp operator in a tryptophane operon derived from *E. coli*; a lac promoter in a lactose operon; a PL and a PR promoters derived from lambda phage; a gluconate synthase promoter (gnt) derived from *Bacillus subtilis*; an alkali protease promoter (apr); a neutral protease promoter (npr); and α-amylase promoter (amy). A uniquely modified and designed sequence such as a tac promoter may be used. A ribosome linkage sequence may be, for example, a sequence derived from *E. coli* or *Bacillus subtilis*, but any sequence may be used as long as it can function in a desired host such as *E. coli* and *Bacillus subtilis*. For example, one can use a consensus sequence formed by DNA synthesis, that is, a sequence with more than 4 consecutive bases complementary to 3'-terminal region in 16S ribosome RNA. A transcription termination sequence is not always necessary, but a ρ-factor independent terminator such as a lipoprotein terminator and a trp operon terminator may be used. Desirably, these control regions on a recombinant plasmid may be sequentially aligned as follows; from upstream of 5'-terminal, a promoter sequence, a ribosome linkage sequence, a nucleoside phosphorylase coding gene and a transcription termination sequence.

As examples of a plasmid herein, pBR 322, pUC18, Bluescript II SK(+), pKK223-3 and pSC101 having an autonomously replicable region in *E. coli*; pUB110, pTZ4, pC194, ρ11, φ1 and φ105 having an autonomously replicable region in *Bacillus subtilis* may be used as a vector. As examples of a plasmid autonomously replicable in two or more hosts, pHV14, TRp7, Yep7 and pBS7 may be used as a vector.

A given host herein may be typically, but not limited to, *Escherichia coli* as described in Examples later, but other strains such as *Bacillus* sp. including *Bacillus subtilis*, yeasts and actinomyces may be used.

Nucleoside phosphorylase activity in this invention may be obtained from, besides the above strains having the enzyme activity, a processed material of the strain exhibiting the enzyme activity and an immobilized product thereof. A processed material of the strain may be, for example, acetone-dried strain or a bacterial debris prepared by an appropriate procedure such as mechanical destruction, ultrasonic disintegration, freezing and thawing, pressurization and depressurization, osmotic pressure method, autolysis, cell-wall decomposition and surfactant treatment. If necessary, the strain may be further purified by ammonium sulfate precipitation, acetone precipitation or column chromatography.

In this invention, a metal cation capable of forming a water-insoluble salt with phosphate ion may be, without restriction, any metal cation which can form a water-insoluble salt with phosphate ion as a byproduct in the reaction and may be precipitated; for example, calcium, magnesium, barium, iron, cobalt, nickel, copper, silver, molybdenum, lead, zinc and lithium ions. Among these, particularly preferable are industrially universal and safe metal ions which do not adversely affect the reaction, e.g., calcium, barium, aluminum and magnesium ions.

A metal cation capable of forming a water-insoluble salt with phosphate ion in this invention may be obtained by adding a salt of a metal cation capable of forming a water-insoluble salt with phosphate ion with at least one anion selected from chloride, nitride, carbonate, sulfate, acetate and hydroxyl ions into the reaction solution. Examples of such a salt include calcium chloride, calcium nitride, calcium carbonate, calcium sulfate, calcium acetate, barium chloride, barium nitride, barium carbonate, barium sulfate, barium acetate, aluminum chloride, aluminum nitride, aluminum carbonate, aluminum sulfate, aluminum acetate, calcium hydroxide, barium hydroxide, aluminum hydroxide, magnesium hydroxide, magnesium chloride, magnesium nitride, magnesium carbonate, magnesium sulfate and magnesium acetate.

Such a metal cation may be present as a salt with a pentose-1-phosphate in the reaction solution; for example, ribose-1-phosphate calcium salt, 2-deoxyribose-1-phosphate calcium salt, 2,3-dideoxyribose-1-phosphate calcium salt, arabinose-1-phosphate calcium salt, ribose-1-phosphate barium salt, 2-deoxyribose-1-phosphate barium salt, 2,3-dideoxyribose-1-phosphate barium salt, arabinose-1-phosphate barium salt, ribose-1-phosphate aluminum salt, 2-deoxyribose-1-phosphate aluminum salt, 2,3-dideoxyribose-1-phosphate aluminum-salt and arabinose-1-phosphate aluminum salt.

A reaction for preparing a nucleoside compound in this invention may be conducted under the conditions such as appropriate pH and temperature and within the control ranges thereof, depending on a target nucleoside, a 1-phosphorylated saccharide derivative and a base as substrates, a nucleoside phosphorylase or a microorganism exhibiting the activity of the enzyme as a reaction catalyst, and the type and the properties of a metal salt added for removing phosphoric acid from the reaction system; generally at pH 5 to 10 and a temperature of 10 to 60° C. If pH is not within the control range, a reaction inversion rate may be reduced due to, for example, poor stability of a target product or substrate, reduction in enzyme activity and failure to forming a water-insoluble salt with phosphoric acid. If pH varies in the course of the reaction, an acid such as hydrochloric acid and sulfuric acid or an alkali such as sodium hydroxide and potassium hydroxide may be, when necessary, added at an appropriate timing. The concentrations of a 1-phosphorylated saccharide derivative and a base are suitably about 0.1 to 1000 mM. In terms of a molar ratio between them, a molar ratio of a base to a 1-phosphorylated saccharide derivative or its salt may be 1 to 10, preferably 0.95 or less in the light of a reaction inversion rate.

A metal salt capable of forming a water-insoluble salt with phosphoric acid added may be added in a molar ratio of 0.1 to 10, more preferably 0.5 to 5 to a 1-phosphorylated saccharide derivative used in the reaction. There are no restrictions to an addition procedure of the salt, and it may be added in one portion or portionwise during the reaction. This invention basically uses water as a solvent, but an organic solvent such as an alcohol and dimethylsulfoxide used in a common enzyme reaction may be, if necessary, added in an appropriate amount. In a reaction with a higher concentration, a base as a substrate or a nucleoside as a product may be not be completely dissolved in the reaction solution. This invention may be also applied to such a case.

A nucleoside compound produced as described above may be isolated by a common procedure such as concentration, crystallization, dissolution, electrodialysis and adsorption and desorption using an ion-exchange resin or charcoal.

EXAMPLES

This invention will be more specifically described with reference to, but not limited to, Examples.

Example 1

Preparation of an anomer mixture of 3,5-O-bis(4-chlorobenzoyl)-2-deoxy-D-ribose-1-phosphate (18) and bis[3,5-O-bis(4-chlorobenzoyl)-2-deoxy-D-ribos-1-yl]phosphate (19)

To a mixture of 1.18 g of orthophosphoric acid in 51 mL of acetonitrile were added 2.3 g of tri-n-butylamine and 5.07 g of molecular sieves 4A, and the mixture was cooled to 5° C. with stirring. After one hour, to the mixture was added 5.07 g of 3,5-O-bis(4-chlorobenzoyl)-2-deoxy-α-D-ribosyl chloride (purity: 85%), and the mixture was stirred for one hour to give a solution of a mixture of the title compounds (18) and (19) [(18):(19)=3:5, α-form/β-form of compound (18)=5/2] in acetonitrile.

For preparing a sample for analysis, these compounds were converted into cyclohexylamine salts, which were then purified by silica gel column chromatography to provide two anomer isomers (19a) and (19b) of the title compound (19) from a fraction eluted with methanol-ethyl acetate (1:10).

(19a): Less polar fraction $^1$H NMR (CDCl$_3$, 270 MHz) d: 8.0–7.8 (m, 8H), 7.4–7.2 (m, 8H), 6.06 (m, 1.2H), 5.98 (m, 0.8H), 5.56 (m, 1.2H), 5.41 (m, 0.8H), 4.7–4.3 (m, 6H), 2.6–2.4 (m, 1H), 2.75–2.6 (m, 2H), 2.5–2.3 (m, 2H), 2.2–1.9 (m, 2H), 1.8–1.6 (m, 2H), 1.6–0.9 (m, 8H); MS (APCI) m/z 883 (M–H). (19b): More polar fraction $^1$H NMR (CDCl$_3$, 270 MHz) d: 8.0–7.8 (m, 8H), 7.4–7.2 (m, 8H), 6.1–5.9 (m, 2H), 5.55 (m, 0.67H), 5.39 (m, 1.33H), 4.7–4.3 (m, 6H), 3.1–2.85 (m, 1H), 2.75–2.4 (m, 2H), 2.32 (m, 2H), 2.2–1.9 (m, 2H), 1.8–1.6 (m, 2H), 1.6–0.9 (m, 8H); MS (APCI) m/z 883 (M–H).

Example 2

Preparation of an anomer mixture of 3,5-O-bis(4-chlorobenzoyl)-2-deoxy-D-ribose-1-phosphate and bis[ 3,5-O-bis(4-chlorobenzoyl)-2-deoxy-D-ribos-1-yl]phosphate To a mixture of 1.11 g of orthophosphoric acid in 49 mL of 2-butanone were added 2.11 g of tri-n-butylamine and 4.9 g of molecular sieves 4A, and the mixture was cooled to 5° C. with stirring. To the mixture was added 4.9 g of 3,5-O-bis(4-chlorobenzoyl)-2-deoxy-α-D-ribosyl chloride (purity: 85%), and the mixture was stirred for 10 min to give a solution of a mixture of the title compounds (18) and (19) [(18): (19)=1:4, α-form/β-form of compound (18)=7/10] in 2-butanone.

Example 3

Preparation of an anomer mixture of 3,5-O-bis(4-chlorobenzoyl)-2-deoxy-D-ribose-1-phosphate and bis[3,5-O-bis(4-chlorobenzoyl)-2-deoxy-D-ribos-1-yl]phosphate To a mixture of 136.8 g of orthophosphoric acid in 2 L of 2-butanone were added 90.6 g of tri-n-butylamine and 200 g of molecular sieves 4A, and the mixture was cooled to 5° C. with stirring. After stirring for one hour, to the mixture was added 200 g of 3,5-O-bis(4-chlorobenzoyl)-2-deoxy-α-D-ribosyl chloride (purity: 85%), and the mixture was stirred for 2 hours to give a solution of a mixture of the title compounds (18) and (19) [(18):(19)=5:4, α-form/β-form of compound (18)=5/2] in 2-butanone.

Example 4

Preparation of 3,5-O-bis(4-chlorobenzoyl)-2-deoxy-α-D-ribose-1-phosphate (18a)

The acetonitrile solution prepared in Example 1 was cooled to 5° C. with stirring, and 2.29 g of orthophosphoric acid was added to the mixture. After stirring for 3 hours, crystallization was initiated and then the mixture became a thick suspension. After 5 hours, the ratio of α-form/β-form of the title compound (18) in the reaction suspension was 10/1. The crystals were collected as a mixture with molecular sieves. The solid was dissolved in 100 mL of methanol and the mixture was again filtrated to remove molecular sieves. HPLC assay showed that 3.68 g of the title compound (18a) was contained in the methanol solution (Yield: 74.6% after reduction from the purity of the starting material) without the β-form on HPLC.

Example 5

Preparation of 3,5-O-bis(4-chlorobenzoyl)-2-deoxy-α-D-robose-1-phosphate (18a)

The 2-butanone solution prepared in Example 2 was cooled to 5° C. with stirring, and 2.2 g of orthophosphoric acid was added to the solution. After stirring for 1 hour, precipitation of crystals initiated and then a thick suspension was obtained. After 20 hours, the ratio of α-form/β-form for compound (18a) in the reaction suspension was 8:1. To the suspension was added 6.33 g of tri-n-butylamine to dissolve the precipitated crystals and molecular sieves were removed by filtration. To the filtrate was added 250 mL of toluene, and the solution was washed with 55 mL of water. The organic layer was ice-cooled. To the mixture was added 2.32 g of cyclohexylamine for crystallization with stirring. After 1 hour, the precipitated crystals were collected by filtration and dried in vacuo at room temperature to provide 3.19 g of a dicyclohexylamine salt of compound (16a) as a colorless powder (Yield: 64.7% after reduction from the purity of the starting material; α-form:β-form=97.5:2.5).

$^1$H NMR (DMSO-d$_6$, 270 MHz) d: 8.00(d, J=8.6 Hz, 2H), 7.96 (d, J=8.6 Hz, 2H), 7.58 (d, J=8.6 Hz, 2H), 7.58 (d, J=8.6 Hz, 2H), 5.82 (dd, J=5.3, 5.3 Hz, 1H), 5. 36 (d, J=8.6 Hz, 1H), 4.6–4.3 (m, 3H), 4.7–3.5 (br, 6H), 2.7–2.6 (m, 2H), 2.55–2.4 (m, 1H), 2.25 (d, J=4.2 Hz, 1H), 1.85–1.75 (m, 4H), 1.7–1.6 (m, 4H), 1.55–1.45 (m, 2H), 1.25–0.9 (m, 10H); MS (APCI) m/z 590 (M+C$_6$H$_{14}$N).

Example 6

Preparation of 3,5-O-bis(4-chlorobenzoyl)-2-deoxy-α-D-robose-1-phosphate (18a)

The 2-butanone solution prepared in Example 3 was cooled to 5° C. with stirring. After stirring for 1 hour, precipitation of crystals initiated and then a thick suspension was obtained. After 23 hours, the ratio of α-form/β-form for compound (18a) in the reaction suspension was 7:1. To the suspension was added 259 g of tri-n-butylamine to dissolve the precipitated crystals and molecular sieves were removed by filtration. The filtrate was washed with 2.2 L of water and the aqueous layer was extracted with 1 L of toluene. The combined organic layer was ice-cooled. To the mixture was added 87.5 g of cyclohexylamine for crystallization with stirring. After 1 hour, the precipitated crystals were collected by filtration and dried in vacuo at room temperature to provide 213 g of a dicyclohexylamine salt of compound (16a) as a colorless powder (Yield: 78.1% after reduction from the purity of the starting material; α-form:β-form=96.9:3.1).

Example 7

Preparation of 2-deoxy-α-D-ribose-1-phosphate (20)

To the methanol solution prepared in Example 4 was added 20 mL of an aqueous solution of ammonium hydroxide, and the mixture was stirred at room temperature. After stirring for 28 hours, the precipitated crystals were collected by filtration and dried in vacuo at room temperature to provide 589 mg of an ammonium salt of compound (20) as a colorless powder (Yield: 21.1% without the β-form on HPLC).

Example 8

Preparation of 2-deoxy-α-D-ribose-1-phosphate (20)

Compound (18a) prepared in Example 6 was suspended in a mixture of 2.3 L of methanol and 450 mL of an aqueous ammonium hydroxide solution, and the mixture was stirred at room temperature. After stirring for 28 hours, the precipitated crystals were collected by filtration and dried in vacuo at room temperature to provide 62.0 g of an ammonium salt of compound (20) as a colorless powder (Yield: 81.0% without the β-form on HPLC).

$^1$H NMR (D$_2$O, 270 MHz) d: 5.56 (s, 1H), 4.03 (m, 2H), 3.52 (dd, J=3.3, 12.2 Hz, 1H), 3.41 (dd, J=5.3, 12.2 Hz, 1H), 2.17 (m, 1H), 1.87 (d, J=13.9 Hz, 1H); MS (APCI) m/z: 213 (M–H).

Example 9

Preparation of 2,3,5-O-tris(4-chlorobenzoyl)-α-D-ribose-1-phosphate (21)

To a mixture of 3.32 g of orthophosphoric acid in 67 mL of methyl isobutyl ketone were added 2.11 g of tri-n-butylamine and 6.6 g of molecular sieves 4A, and the mixture was cooled to 5° C. with stirring. To the mixture was added 6.66 g of 2,3,5-O-tris(4-chlorobenzoyl)-α-D-ribosyl chloride. After 1 hour, precipitation of crystals initiated and then a thick suspension was provided. After 10 hours, the ratio of α-form/β-form for compound (19) in the reaction suspension was 10:1. To the suspension was added 6.33 g of tri-n-butylamine to dissolve the precipitated crystals and molecular sieves were removed by filtration. The filtrate was washed with 55 mL of water. The organic layer was ice-cooled. To the mixture was added 2.4 g of cyclohexylamine for crystallization with stirring. After 1 hour, the precipitated crystals were collected by filtration and dried in vacuo at room temperature to provide 7.02 g of a dicyclohexylamine salt of compound (21) as a colorless powder (Yield: 73.0%; α-form:β-form =99:1).

$^1$H NMR (DMSO-d$_6$, 270 MHz) d: 8.2–7.8 (m, 6H), 7.6–7.4 (m, 6H), 5.9–5.7 (m, 1H), 5.6–5.4 (m, 3H), 4.6–4.3 (m, 1H), 4.7–3.5 (br, 6H), 2.7–2.6 (m, 2H), 1.9–1.7 (m, 4H), 1.7–1.6 (m, 4H), 1.55–1.4 (m, 2H), 1.3–0.9 (m, 10H); MS (APCI) m/z 745 (M+C$_6$H$_{14}$N).

Example 10

Preparation of α-D-ribose-1-phosphate (22)

Compound (21) prepared in Example 9 was suspended in a mixture of 105 mL of methanol and 21 mL of an aqueous ammonium hydroxide solution, and the mixture was stirred at room temperature. After stirring for 32 hours, the precipitated crystals were collected by filtration and dried in vacuo at room temperature to provide 1.90 g of an ammonium salt of compound (22) as a colorless powder (Yield: 86.0% without the β-form on HPLC).

$^1$H NMR (D$_2$O, 270 MHz) d: 5.6 (m, 1H), 4.2 (m, 1H), 4.1–4.0 (m, 2H), 3.75 (m, 1H), 3.7 (m, 1H); MS (APCI) m/z: 229 (M–H).

Example 11

Preparation of 5-O-(4-chlorobenzoyl)-2,3-dideoxy-α-D-ribose-1-phosphate (23)

To a mixture of 3.5 g of orthophosphoric acid in 33 mL of acetonitrile were added 2.2 g of tri-n-butylamine and 3.3 g of molecular sieves 4A, and the mixture was cooled to 5° C. with stirring. To the mixture was added 3.28 g of 5-O-(4-chlorobenzoyl)-2,3-dideoxy-α-D-ribosyl chloride. After 1 hour, precipitation of crystals initiated and then a thick suspension was provided. After 20 hours, the ratio of α-form/β-form for compound (23) in the reaction suspension was 10:1. To the suspension was added 6.5 g of tri-n-butylamine to dissolve the precipitated crystals and molecular sieves were removed by filtration. The filtrate was diluted with 70 mL of toluene and then washed with 55 mL of water. The organic layer was ice-cooled. To the mixture was added 2.5 g of cyclohexylamine for crystallization with stirring. After 1 hour, the precipitated crystals were collected by filtration and dried in vacuo at room temperature to provide 4.56 g of a dicyclohexylamine salt of compound (23) as a colorless powder (Yield: 71.5%; α-form:β-form=97:3).

¹H NMR (DMSO-d$_6$, 270 MHz) d: 8.2–7.8 (m, 2H), 7.6–7.4 (m, 2H), 5.9–5.7 (m, 1H), 5.6–5.4 (m, 1H), 4.6–4.3 (m, 1H), 4.7–3.5 (br, 6H), 2.7–2.6 (m, 2H), 1.9–1.7 (m, 8H), 1.7–1.6 (m, 4H), 1.55–1.4 (m, 2H), 1.3–0.9 (m, 10H); MS (APCI) m/z 374 (M+C$_6$H$_{14}$N).

Example 12

Preparation of 2,3-dideoxy-α-D-ribose-1-phosphate (24)

Compound (23) prepared in Example 11 was suspended in a mixture of 46 mL of methanol and 10 mL of an aqueous ammonium hydroxide solution, and the mixture was stirred at room temperature. After stirring for 30 hours, the precipitated crystals were collected by filtration and dried in vacuo at room temperature to provide 1.68 g of an ammonium salt of compound (24) as a colorless powder (Yield: 85.0% without the β-form on HPLC).

¹H NMR (D$_2$O, 270 MHz) d: 5.2 (m, 1H), 4.1–3.9 (m, 1H), 3.6–3.3 (m, 2H), 2.1–2.3 (m, 2H), 1.9–1.7 (m, 2H); MS (APCI) m/z: 197 (M–H).

Example 13

Preparation of 2,3,5-O-tris(4-chlorobenzoyl)-α-D-arabinofuranosyl-1-phosphate (25)

To a mixture of 3.3 g of orthophosphoric acid in 67 mL of methyl isobutyl ketone were added 2.1 g of tri-n-butylamine and 6.6 g of molecular sieves 4A, and the mixture was cooled to 5° C. with stirring. To the mixture was added 6.6 g of 2,3,5-O-tris(4-chlorobenzoyl)-α-D-arabinofuranosyl chloride. After 1 hour, precipitation of crystals initiated and then a thick suspension was provided. After 8 hours, the ratio of α-form/β-form for compound (25) in the reaction suspension was 10:1. To the suspension was added 6.3 g of tri-n-butylamine to dissolve the precipitated crystals and molecular sieves were removed by filtration. The filtrate was washed with 55 mL of water. The organic layer was ice-cooled. To the mixture was added 2.4 g of cyclohexylamine for crystallization with stirring. After 1 hour, the precipitated crystals were collected by filtration and dried in vacuo at room temperature to provide 6.72 g of a dicyclohexylamine salt of compound (25) as a colorless powder (Yield: 70.5%; α-form:β-form=99:1).

MS (APCI) m/z 745 (M+C$_6$H$_{14}$N).

Example 14

Preparation of α-D-arabinofuranosyl-1-phosphate (26)

Compound (25) prepared in Example 13 was suspended in a mixture of 94 mL of methanol and 18 mL of an aqueous ammonium hydroxide solution, and the mixture was stirred at room temperature. After stirring for 48 hours, the precipitated crystals were collected by filtration and dried in vacuo at room temperature to provide 1.72 g of an ammonium salt of compound (26) as a colorless powder (Yield: 82.0% without the β-form on HPLC).

¹H NMR (D$_2$O, 270 MHz) d: 5.3 (m, 1H), 3.95–3.3 (m, 5H); MS (APCI) m/z: 229 (M–H).

Example 15

Preparation of (2R)-2-benzyloxymethyl-1,3-dioxorane-4-phosphate (27)

To a solution of 1.06 g of (2R)-2-benzyloxymethyl-4-(R,S)-acetoxy-1,3-dioxorane in 12 mL of ether under ice-cooling was added 4 mL of a 4N solution of hydrochloric acid in dioxane. After stirring 3.5 hours, the mixture was warmed to room temperature. After removing the solvent by concentration, the residue was further subject to azeotropy with toluene to give 500 mg of (2R)-2-benzyloxymethyl-1,3-dioxoranyl chloride as a colorless and transparent oil. To 1.1 mL of acetonitrile were sequentially added 0.27 g of orthophosphoric acid, 0.66 mL of tri-n-butylamine and 0.23 g of molecular sieves 4A, and the mixture was stirred for 1.5 hours. To the suspension under ice-cooling was added 0.27 g of the previous oil, and the mixture was stirred under ice-cooling for 5.5 hours. To the mixture was added 0.6 mL of tri-n-butylamine. After stirring for 30 min, the mixture was diluted with toluene and extracted with water. The aqueous layer was extracted with n-butanol and then concentrated. The concentrate was dissolved in toluene, and to the solution was added cyclohexylamine to give a cyclohexylamine salt of compound (27) as a white solid.

¹H-NMR (D$_2$O) δ: 0.98–1.10 (2H, m), 1.14–1.23 (6H, m), 1.47–1.51 (2H, m), 1.61–1.64 (4H, m), 1.78–1.83 (4H, m), 2.94–3.00 (2H, m), 3.46–3.60 (2H, m), 3.72–3.79 (1H, m), 3.92–4.00 (1H, m), 4.41–4.51 (2H, m), 5.01–5.03 and 5.22–5.24 (total 1H, m), 5.64–5.72 (total 1H, m), 7.24–7.30 (5H, m); MS (APCI) m/z: 390 (M+C$_6$H$_{14}$N)$^+$.

Example 16

Preparation of (2R)-2-hydroxymethyl-1,3-dioxorane-4-phosphate (28)

In 10 mL of methanol was dissolved 0.2 g of compound (27) prepared in Example 15. The solution was subject to hydrogenation under an ambient pressure using 0.11 g of 10% Pd/C as a catalyst. After removing the catalyst by filtration, the filtrate was concentrated to give a cyclohexylamine of compound (28).

¹H-NMR (D$_2$O) δ: 0.99–1.06 (2H, m), 1.10–1.24 (6H, m), 1.47–1.50 (2H, m), 1.62–1.66 (4H, m), 1.80–1.85 (4H, m), 1.96–3.02 (2H, m), 3.51–3.57 (2H, m), 3.72–3.79 (1H, m), 3.93–4.00 (1H, m), 4.99–5.01 and 5.13–5.15 (total 1H, m), 5.64–5.67 and 5.70–5.73 (total 1H, m); MS (APCI) m/z: 199 (M–H)$^-$.

Example 17

Preparation of 2,3-dideoxy-3-fluoro-5-O-(4-phenylbenzoyl)-α-D-erythropentofuranose-1-phosphate (29)

Seventy mg of molecular sieves 4A was added to a stirred mixture of 62 mg of orthophosphoric acid, 52 μL of tri-n-butylamine and 0.7 mL of acetonitrile at room temperature, and the mixture was stirred in an ice-bath. To the mixture was added 70 mg of 2,3-dideoxy-3-fluoro-5-O-(4-phenylbenzoyl)-D-erythropentofuranosyl chloride, and the mixture was reacted at the same temperature for 1 day. Then, to the mixture were added 156 μL of tri-n-butylamine and then deionized water. The mixture was extracted with toluene three times. To the organic layer was added 48 μL of cyclohexylamine and the mixture was stirred for 30 min. The mixture was concentrated in vacuo, and acetone was added to form a precipitate, which was collected by filtration. The residue was washed with chloroform and dried in vacuo at room temperature to give a dicyclohexylamine of compound (29) as a white solid.

¹H-NMR (CD$_3$OD) δ: 1.1–1.4 (10H, m), 1.65 (2H, m), 1.89 (4H, m), 1.96 (4H, m), 2.3–2.5 (2H, m), 2.91 (2H, m), 4.5 (2H, m), 4.6–4.8 (1H, m), 5.1–5.3 (1H, m), 5.97 (1H, m), 7.41 (1H, m), 7.47 (2H, m), 7.68 (2H, m), 7.75 (2H, m), 8.08 (2H, m); MS (APCI) m/z: 496 (M+$C_6H_{14}$N)$^+$.

Example 18

Preparation of 2,3-dideoxy-3-fluoro-α-D-erythropentofuranose-1-phophate (30)

To a solution of 21 mg of compound (29) prepared in Example 17 in 1 mL of methanol was added 20 μL of cyclohexylamine and the mixture was reacted for 2 weeks. The mixture was concentrated in vacuo and diethyl ether was added. The mixture was filtered, and the solid was dried in vacuo to give 12 mg of a dicyclohexylamine salt of the title compound as a white solid.

$^1$H-NMR (CD$_3$OD) δ: 1.1–1.4 (10H, m), 1.66 (2H, m), 1.79 (4H, m), 1.94 (4H, m), 2.3–2.4 (2H, m), 2.88 (2H, m), 3.59 (2H, m), 4.3–4.4 (1H, m), 5.11 (0.5H, m; the other 0.5H was undistinguishable because it was behind the peak of water), 5.89 (1H, m); MS (APCI) m/z: 215 (M–H)$^-$.

Example 19

Preparation of 2,3-dideoxy-3-fluoro-5-O-(4-phenylbenzoyl)-D-erythropentofuranose-1-phosphate (31)

At room temperature 0.86 g of molecular sieves 4A was added to a stirred mixture of 759 mg of orthophosphoric acid, 646 μL of tri-n-butylamine and 8.6 mL of acetonitrile at room temperature, and the mixture was stirred in an ice-bath. To the mixture was added 864 mg of 2,3-dideoxy-3-fluoro-5-O-(4-phenylbenzoyl)-D-erythropentofuranosyl chloride, and the mixture was reacted at the same temperature for 1 day. Then, to the mixture were added 1.94 mL of tri-n-butylamine and then deionized water. The mixture was extracted with toluene three times and washed with purified water five times. The organic layer was separated. To the organic layer was added 590 μL of cyclohexylamine and the mixture was stirred for 30 min. The mixture was concentrated in vacuo. After addition of acetone, the mixture was stirred and filtrated. The residue was further washed with isopropyl ether and dried in vacuo at room temperature to give compound (31) as a white solid. α-form:β-form=66:34.

$^1$H-NMR (CD$_3$OD) δ: 1.1–1.4 ppm (10H, m), 1.66 (2H, m), 1.78 (4H, m), 1.98 (4H, m), 2.3–2.6 (2H, m), 2.89 (2H, m), 4.44 & 4.46 (α & β, 2H), 4.6–4.8 (1H, m), 5.1–5.3 & 5.3–5.4 (α & β, 1H, m), 5.97 & 6.00 (α & β,1H, m), 7.40 (1H, m), 7.47 (2H, m), 7.68 (2H, m), 7.75 (2H, m), 8.07 (1H, m), 8.13 (1H, m).

Example 20

Preparation of 2,3-dideoxy-3-fluoro-D-erythropentofuranose-1-phophate (32)

To a solution of 0.29 g of compound (31) prepared in Example 19 in 15 mL of methanol was added 279 μL of cyclohexylamine and the mixture was reacted for 1 week. The mixture was concentrated in vacuo and diethyl ether was added. After stirring, the mixture was filtered, and the solid was dried in vacuo to give 185 mg of a dicyclohexylamine salt of compound (32) as a white solid. α-form:β-form=66:34.

$^1$H-NMR (CD$_3$OD) δ: 1.1–1.4 ppm (10H, m), 1.67 (2H, m), 1.79 (4H, m), 2.2–2.4 (2H, m), 2.94 (2H, m), 3.59 & 3.62 (a & 1,2H, m), 3.3–3.4 (2H, m), 5.10 & 5.1–5.24 (α & β, 0.5H & 1H, m, 0.5H of the αform was undistinguishable because the signal was behind the peak of water), 5.88 & 5.93 (α & β, 1H, m).

Example 21

Preparation of 3,5-O-dibenzoyl-2-O-methylribose-1-phosphate (33)

To 2.84 g of 1,3,5-O-tribenzoyl-2-O-methyl-α-D-ribose was added 14.5 mL of a 4N solution of hydrochloric acid in dioxane, and the mixture was stirred under ice-cooling. After stirring 2.5 hours, 10 mL of a 4N solution of hydrochloric acid in dioxane was further added, and the mixture stirred for 1 hour. After evaporating the solvent, the residue was further subject to azeotropy with 10 mL of dioxane twice to give 3,5-O-dibenzoyl-2-O-methylribosyl-1-chloride. Separately, 2.98 g of 98% phosphoric acid was dissolved in 15 mL of 4-methyl-2-pentanone and after adding 2.8 g of molecular sieves 4A, the mixture was stirred for 30 min. To the mixture were added 1.42 mL of tri-n-butylamine and then a solution of the previous 3,5-O-dibenzoyl-2-O-methylribosyl-1-chloride in 10 mL of 4-methyl-2-pentanone. After reacting the mixture at room temperature for 20 hours, it was neutralized with 7.1 mL of tri-n-butylamine. After removing the molecular sieves by filtration, the filtrate was washed with 20 mL of water three times. The organic layer was evaporated and purified by silica gel column chromatography to give 950 mg of compound (33).

MS (APCI) m/z: 451 (M–H)$^-$; IR (KBr) cm$^{-1}$: 3448, 2963, 1721, 1453, 1278, 1111, 976, 711, 558.

Example 22

Preparation of 2-O-methylribose-1-β-phosphate (34)

To 850 mg of compound (33) prepared in Example 21 was 20 mL of 14% ammonia-methanol, and the mixture was reacted at room temperature for 20 hours. After evaporation of the solvent, diisopropyl ether was added to form a sludge and the crystalline powder was collected by filtration. The powder was dissolved in methanol. To the solution was added cyclohexylamine, and the mixture was stirred. After evaporating methanol, diisopropyl ether was added to the residue to form a sludge. The crystalline powder was collected by filtration and washed with diisopropyl ether. The desired product was extracted with water and the aqueous layer was washed with 4-methyl-2-pentanone twice. The aqueous layer was concentrated and to the layer was added diisopropyl ether to form a sludge. After filtration, the crystals were washed with diisopropyl ether to give 120 mg of a dicyclohexylamine salt of compound (34).

$^1$H-NMR (D$_2$O) δ: 3.37 (s, 3H), 3.49 (dd, 1H, J=4.9 Hz, 12.7 Hz), 3.62 (d, 1H, J=4.9 Hz), 3.69 (dd, 1H, J=2.7 Hz, 12.7 Hz), 3.74–3.78 (m, 1H), 4.28 (dd, 1H, J=4.6 Hz, 7.8 Hz), 5.39 (d, 1H, J=5.9 Hz); MS (APCI) m/z: 243 (M–H)$^-$.

Example 23

Preparation of 3,5-O-bis(4-chlorobenzoyl)-2-deoxy-α-D-ribose-1-phosphate (18a)

To a mixture of 6.92 g of orthophosphoric acid in 80 mL of acetonitrile were added 5.51 mL of tri-n-butylamine and 10 g of molecular sieves 4A. The mixture was stirred at room temperature for 5 hours and allowed to stand overnight. After cooling to −7° C., to the mixture was added 10 g of 3,5-O-bis(4-chlorobenzoyl)-2-deoxy-α-D-ribosyl chloride (purity: 85%). The mixture was stirred for 9 hours and allowed to stand at −15° C. overnight. After adding 16.5 mL of tri-n-butylamine, the molecular sieves were removed by filtration. The filtrate was concentrated and the residue was dissolved in 4-methyl-2-pentanone and washed with water. The organic layer was ice-cooled and 5.66 mL of cyclohexylamine was added with stirring for crystallization. After 1.5 hours, the precipitated crystals were filtered and dried in vacuo at room temperature to give 13.5 g of a dicyclohexylamine salt of compound (18a). α-form:β-form=98.8:1.2).

Example 24

Preparation of 2-deoxy-α-D-ribose-1-phosphate (20)

To a solution of 7.05 g of the compound obtained in Example 23 in methanol was added 2.92 mL of cyclohexylamine, and the mixture was stirred at room temperature. After stirring 72 hours, the mixture was concentrated and to the residue was added ethanol to provide a suspension which was then stirred. After collecting the precipitated crystals, they were dried I vacuo at room temperature to give 3.87 g of a dicylcohexylamine salt of compound (20) (without the β-form on NMR).

$^1$H NMR (D$_2$O) d: 5.57 (dd, J=5.1, 6.1 Hz, 1H), 4.03 (m, 2H), 3.54 (ddd, J=1.2, 2.2, 12.2 Hz, 1H), 3.42 (ddd, J=1.2, 5.1, 12.2 Hz, 1H), 3.18–2.94 (m, 2H), 2.17 (m, 1H), 1.90 (d, J=1.2, 12.8 Hz, 1H), 1.8–1.45 (m, 10H), 1.25–0.9 (m, 12H).

Anal. Calcd. for C$_5$H$_9$O$_7$P.C$_{12}$H$_{28}$N$_2$, C: 49.50%; H: 9.04%; N: 6.79%; P: 7.51%, Found C: 49.26%; H: 8.81%; N: 6.64%; P: 7.29%.

Example 25

Preparation of 2'-deoxyadenosine (1)

Fifty mL of an LB medium was inoculated with *Escherichia coli* K-12/XL-10 strain (Stratagene Inc.) and it was cultured at 37° C. overnight. After collection, the bacteria was lysed with a lysis solution containing 1 mg/mL of lysozyme. The lysis solution was treated with phenol and DNA was precipitated as usual by ethanol precipitation. The DNA precipitate was collected with a glass rod and washed to prepare an *E. coli* chromosome DNA.

Oligonucletides of SEQ ID Nos. 1 and 2 designed based on the sequence a known deoD gene in *Escherichia coli* (GenBank accession No. AE000508 with a coding region of base numbers 11531 to 12250) were used as primers for PCR. These primers have restriction enzyme recognition sequences for EcoRI and Hind III near 5'- and 3'-ends, respectively.

SEQ ID No. 1: GTGAATTCAC AAAAAGGATA AAACAATGGC

SEQ ID No. 2: TCGAAGCTTG CGAAACACAA TTACTCTTT

Using 0.1 mL of a PCR reaction solution containing 6 ng/μL of the above *E. coli* chromosome DNA completely digested by restriction enzyme Hind III and the primers (each at 3 μM), PCR was conducted by 30 cycles under the conditions of denaturation: 96° C., 1 min; annealing: 55° C., 1 min; elongation: 74° C., 1 min per a cycle.

The above reaction product and a plasmid pUC18 (Takara Shuzo Co. Ltd.) were digested by EcoRI and Hind III and ligated using Ligation-High (Toyobo Co. Ltd.). The recombinant plasmid obtained was used to transform *Escherichia coli* DH5α. The transformed strain was cultured in an LB agar medium containing 50 μg/mL of ampicillin and X-Gal (5-bromo-4-chloro-3-indolyl-β-galactoside) to provide an Am-resistant transformant as a white colony. A plasmid was extracted from the transformant thus obtained and the plasmid in which a desired DNA fragment had been inserted was designated as pUC—PNP73. The transformant thus obtained was designated as *Escherichia coli* MT-10905.

*Escherichia coli* MT-10905 was cultured by shaking at 37° C. overnight in 100 mL of an LB medium containing 50 μg/mL of Am. The culture medium was centrifuged at 13,000 rpm for 10 min to collect the bacteria. The bacteria were suspended in 10 mL of 10 mM Tris-hydrochloride buffer (pH 8.0) and ultrasonicated to give a homogenate which was then used as an enzyme source.

Reaction solutions were prepared by adding calcium chloride (Waco Pure Chemicals, Extra pure grade) at different concentrations to a mixture of 2.5 mM 2-deoxy-α-D-ribose-1-phosphate diammonium salt prepared in Example 8, 2.5 mM adenine (Wako Pure Chemicals, Extra pure grade), 0.1 mL of the ultrasonic enzyme homogenate from a purinenucleoside-phosphorylase producing strain and 10 mM Tris-hydrochloride buffer (pH 7.4). One mL of a reaction solution was reacted at 30° C. for 24 hours. At the end of the reaction, a white precipitate had been formed.

HPLC analysis described below for a post-reaction solution showed a peak completely identical to the peak of 2'-deoxyadenosine (Wako Pure Chemicals, Extra pure grade) in all the post-reaction solutions.

HPLC Analysis Conditions
Column: YMC-Pack ODS—A312, 150×6.0 mm I.D.
Column temperature: 40° C.
Pump flow rate: 0.75 mL/min
Detection: UV 260 nm
Eluent: 10 mM phosphoric acid:acetonitrile=95:5 (V/V)

Table 1 shows the calculation results of a reaction inversion rate after determining a concentration of 2'-deoxyadenosine in a post-reaction solution.

TABLE 1

| Amount of calcium chloride (mM) | Reaction inversion rate (%) |
|---|---|
| 0.0 | 80.4 |
| 2.5 | 90.8 |
| 10.0 | 96.0 |

Example 26

Preparation of 2'-deoxyadenosine (2)

A reaction was conducted as described in Example 25 except that aluminum chloride was added in place of calcium chloride. At the end of the reaction, a white precipitate had been formed. HPLC analysis for the post-reaction solutions as described in Example 25 showed a peak completely identical to the peak of 2'-deoxyadenosine (Wako Pure Chemicals, Extra pure grade) in all the post-reaction solutions. Table 2 shows the calculation results of a reaction inversion rate after determining a concentration of 2'-deoxyadenosine in a post-reaction solution.

TABLE 2

| Amount of calcium chloride (mM) | Reaction inversion rate (%) |
|---|---|
| 0.0 | 80.4 (same as in Example 15) |
| 2.5 | 90.2 |
| 10.0 | 93.3 |

Example 27

Preparation of 2'-deoxyadenosine (3)

A reaction was conducted as described in Example 25 except that 10 mM of barium chloride was added in place of calcium chloride. At the end of the reaction, a white precipitate had been formed. HPLC analysis for the post-reaction solutions as described in Example 25 showed a peak completely identical to the peak of 2'-deoxyadenosine (Wako Pure Chemicals, Extra pure grade) in the post-reaction solutions. A reaction inversion rate after determining a concentration of 2'-deoxyadenosine in a post-reaction solution was calculated to be 92.4%.

Example 28

Preparation of Thymidine

One mL of a reaction solution consisting of 2.5 mM 2-deoxy-α-D-ribose-1-phosphate diammonium salt prepared in Example 8, 2.5 mM thymine (Wako Pure Chemicals, Extra pure grade), 12 units/mL thymidine phosphorylase (SIGMA), 0 mM or 10 mM calcium nitrate (Wako Pure Chemicals, Extra pure grade) and 10 mM Tris-hydrochloride buffer (pH 7.4) was reacted at 30° C. for 24 hours. At the end of the reaction, a white precipitate had been formed. HPLC analysis for the post-reaction solutions as described in Example 25 showed a peak completely identical to the peak of thymidine (Wako Pure Chemicals, Extra pure grade) in the post-reaction solution. Table 3 shows the calculation results of a reaction inversion rate after determining a concentration of thymidine in the post-reaction solution.

TABLE 3

| Amount of calcium chloride (mM) | Amount of thymidine formed (mM) |
|---|---|
| 0 | 75.2 |
| 10.0 | 91.2 |

Example 29

Preparation of 2'-deoxyadenosine (4)

One mL of a reaction solution consisting of 100 mM 2-deoxy-α-D-ribose-1-phosphate diammonium salt prepared in Example 8, 100 mM adenine (Wako Pure Chemicals, Extra pure grade), 0.1 mL of the ultrasonic enzyme homogenate from a purinenucleoside-phosphorylase producing strain prepared in Example 25, 0 to 150 mM calcium chloride (Waco Pure Chemicals, Extra pure grade) and 100 mM Tris-hydrochloride buffer (pH 8.0) was reacted at 50° C. for 24 hours. At the end of the reaction, a white precipitate had been formed. HPLC analysis for the post-reaction solutions as described in Example 25 showed a peak completely identical to the peak of 2-deoxyadenosine (Wako Pure Chemicals, Extra pure grade) in the post-reaction solutions. Table 4 shows the calculation results of determining a concentration of 2'-deoxyadenosine in a post-reaction solution.

TABLE 4

| Amount of calcium chloride (mM) | Amount of 2'-deoxyadenosine formed (mM) |
|---|---|
| 0 | 85.0 |
| 20 | 90.0 |
| 60 | 96.5 |
| 100 | 97.8 |
| 150 | 97.5 |

Example 30

Preparation of 2'-deoxyguanosine

One mL of a reaction solution consisting of 100 mM 2-deoxy-α-D-ribose-1-phosphate diammonium salt prepared in Example 8, 100 mM guanine (Wako Pure Chemicals, Extra pure grade), 0.1 mL of the ultrasonic enzyme homogenate from a purinenucleoside-phosphorylase producing strain prepared in Example 25, 0 mM or 150 mM calcium chloride (Waco Pure Chemicals, Extra pure grade) and 100 mM Tris-hydrochloride buffer (pH 8.0) was reacted at 50° C. for 24 hours. At the end of the reaction, a white precipitate had been formed. HPLC analysis for the post-reaction solution as described in Example 25 showed a peak completely identical to the peak of 2-deoxyguanosine (Wako Pure Chemicals, Extra pure grade) in the post-reaction solution. Table 5 shows the calculation results of determining a concentration of 2'-deoxyguanosine in the post-reaction solution.

TABLE 5

| Amount of calcium chloride (mM) | Amount of 2'-deoxyguanosine formed (mM) |
|---|---|
| 0 | 50.0 |
| 150 | 97.5 |

Example 31

Preparation of Adenosine

One mL of a reaction solution consisting of 100 mM α-D-ribose-1-phosphate diammonium salt prepared in Example 10, 100 mM adenine (Wako Pure Chemicals, Extra pure grade), 0.1 mL of the ultrasonic enzyme homogenate from a purinenucleoside-phosphorylase producing strain prepared in Example 25, 0 mM or 150 mM calcium chloride (Waco Pure Chemicals, Extra pure grade) and 100 mM Tris-hydrochloride buffer (pH 8.0) was reacted at 50° C. for 24 hours. At the end of the reaction, a white precipitate had been formed. HPLC analysis for the post-reaction solution as described in Example 25 showed a peak completely identical to the peak of adenosine (Wako Pure Chemicals, Extra pure grade) in the post-reaction solution. Table 6 shows the calculation results of determining a concentration of adenosine in the post-reaction solution.

TABLE 6

| Amount of calcium chloride (mM) | Amount of adenosine formed (mM) |
|---|---|
| 0 | 86.1 |
| 150 | 98.4 |

Example 32

Preparation of 2',3'-dideoxyadenosine

One mL of a reaction solution consisting of 100 mM 2,3-dideoxy-α-D-ribose-1-phosphate diammonium salt prepared in Example 12, 100 mM adenine (Wako Pure Chemicals, Extra pure grade), 0.1 mL of the ultrasonic enzyme homogenate from a purinenucleoside-phosphorylase producing strain prepared in Example 25, 0 mM or 150 mM calcium chloride (Waco Pure Chemicals, Extra pure grade) and 100 mM Tris-hydrochloride buffer (pH 8.0) was reacted at 50° C. for 24 hours. At the end of the reaction, a white precipitate had been formed. HPLC analysis for the post-reaction solution as described in Example 25 showed a peak completely identical to the peak of 2',3'-dideoxyadenosine (Sigma, Extra pure grade) in the post-reaction solution. Table 7 shows the calculation results of determining a concentration of 2',3'-dideoxyadenosine in the post-reaction solution.

TABLE 7

| Amount of calcium chloride (mM) | Amount of 2,3'-dideoxy-adenosine formed (mM) |
|---|---|
| 0 | 82.4 |
| 150 | 96.4 |

Example 33

Preparation of adenine-9-β-D-arabinoside

One mL of a reaction solution consisting of 100 mM α-D-arabinofuranosyl-1-phosphate diammonium salt prepared in Example 14, 100 mM adenine (Wako Pure Chemicals, Extra pure grade), 0.1 mL of the ultrasonic enzyme homogenate from a purinenucleoside-phosphorylase producing strain prepared in Example 25, 0 mM or 150 mM calcium chloride (Waco Pure Chemicals, Extra pure grade) and 100 mM Tris-hydrochloride buffer (pH 8.0) was reacted at 50° C. for 24 hours. At the end of the reaction, a white precipitate had been formed. HPLC analysis for the post-reaction solution as described in Example 25 showed a peak completely identical to the peak of adenine-arabinoside (Sigma, Extra pure grade) in the post-reaction solution. Table 8 shows the calculation results of determining a concentration of adenine-9-β-D-arabinoside in the post-reaction solution.

TABLE 8

| Amount of calcium chloride (mM) | Amount of adenine-9-β-D-arabinoside formed (mM) |
|---|---|
| 0 | 79.4 |
| 150 | 93.4 |

Example 34

Preparation of 2-amino-6-chloropurine-2'-deoxy-β-D-riboside

One mL of a reaction solution consisting of 10 mM 2-deoxy-α-D-ribose-1-phosphate diammonium salt prepared in Example 8, 10 mM 2-amino-6-chloropurine (Tokyo Kasei), 100 mM Tris-hydrochloride buffer (pH 7.5) and 50 μL of the ultrasonic enzyme homogenate from a purine-nucleoside-phosphorylase producing strain prepared in Example 25 was reacted at 50° C. for 4 hours. At the end of the reaction, a white precipitate had been formed. HPLC analysis for the post-reaction solution under the conditions below showed a peak of 2-amino-6-chloropurine-2'-deoxy-β-D-riboside. A reaction inversion rate was calculated to be 20.9% after determining the concentration of 2-amino-6-chloropurine-2'-deoxy-β-D-riboside in the post-reaction solution.

HPLC Analysis Conditions
  Column: Develosil ODS-MG-5, 250×4.6 mm I.D.
  Column temperature: 40° C.
  Pump flow rate: 1.0 mL/min
  Detection: UV 254 nm
  Eluent: 25 mM potassium dihydrogen phosphate:methanol=875:125 (V/V)

Example 35

Preparation of 2,6-diaminopurine-2'-deoxy-β-D-riboside

A reaction was conducted as described in Example 34 except that 2,6-diaminopurine (Tokyo Kasei) was added in place of 2-amino-6-chloropurine. HPLC analysis for the post-reaction solution as described in Example 34 showed a peak of 2,6-diaminopurine-2'-deoxy-β-D-riboside. A reaction inversion rate was calculated to be 75.5% after determining the concentration of 2,6-diaminopurine-2'-deoxy-β-D-riboside in the post-reaction solution.

Example 36

Preparation of 6-mercaptopurine-2'-deoxy-β-D-riboside

A reaction was conducted as described in Example 34 except that 6-mercaptopurine (KOUJIN) was added in place of 2-amino-6-chloropurine. HPLC analysis for the post-reaction solution as described in Example 34 showed a peak of 6-mercaptopurine-2'-deoxy-β-D-riboside. A reaction inversion rate was calculated to be 57.2% after determining the concentration of 6-mercaptopurine-2'-deoxy-β-D-riboside in the post-reaction solution.

Example 37

Preparation of 2-amino-6-iodopurine-2'-deoxy-β-D-riboside

A reaction was conducted as described in Example 34 except that 2-amino-6-iodopurine was added in place of 2-amino-6-chloropurine. HPLC analysis for the post-reaction solution as described in Example 34 showed a peak of 2-amino-6-iodopurine-2'-deoxy-β-D-riboside. A reaction inversion rate was calculated to be 69.2% after determining the concentration of 2-amino-6-iodopurine-2'-deoxy-β-D-riboside in the post-reaction solution.

Example 38

Preparation of 2-acetylamino-6-hydroxypurine-2'-deoxy-β-D-riboside

A reaction was conducted as described in Example 34 except that 2-acetylamino-6-hydroxypurine (Tokyo Kasei) was added in place of 2-amino-6-chloropurine. HPLC analysis for the post-reaction solution under the conditions described below showed a peak of 2-acetylamino-6-hydroxypurine-2'-deoxy-β-D-riboside. A reaction inversion rate was calculated to be 48.7% after determining the concentration of 2-acetylamino-6-hydroxypurine-2'-deoxy-β-D-riboside in the post-reaction solution.

HPLC Analysis Conditions
   Column: Develosil ODS-MG-5, 250×4.6 mm I.D.
   Column temperature: 40° C.
   Pump flow rate: 1.0 mL/min
   Detection: UV 254 nm
   Eluent: 25 mM potassium dihydrogen phosphate:methanol=75:25 (V/V)

Example 39

Preparation of 2-amino-6-cyclopropylaminopurine-2'-deoxy-β-D-riboside

A reaction was conducted as described in Example 34 except that 2-amino-6-cyclopropylaminopurine was added in place of 2-amino-6-chloropurine. HPLC analysis for the post-reaction solution as described in Example 38 showed a peak of 2-amino-6-cyclopropylaminopurine-2'-deoxy-β-D-riboside. A reaction inversion rate was calculated to be 87.6% after determining the concentration of 2-amino-6-cyclopropylaminopurine-2'-deoxy-β-D-riboside in the post-reaction solution.

Example 40

Preparation of 2',3'-dideoxy-3'-fluoro-D-guanosine

One mL of a reaction solution consisting of 7.0 mM 2,3-dideoxy-3-fluoro-D-erythropentofuranose-1-phosphate prepared in Example 18, 10 mM guanine (Tokyo Kasei), 100 mM Tris-hydrochloride buffer (pH 7.5) and 0.1 mL of the ultrasonic enzyme homogenate from a purinenucleoside-phosphorylase producing strain prepared in Example 25 was reacted at 50° C. for 114 hours. HPLC analysis for the post-reaction solution as described in Example 34 showed a peak of 2',3'-dideoxy-3'-fluoro-D-guanosine. A reaction inversion rate was calculated to be 47.7% after determining the concentration of 2',3'-dideoxy-3$^1$-fluoro-D-guanosine in the post-reaction solution.

Example 41

Preparation of 2',3'-dideoxy-3'-fluoro-D-guanosine

One mL of a reaction solution consisting of 7.0 mM 2,3-dideoxy-3-fluoro-D-erythropentofuranose-1-phosphate prepared in Example 18, 10 mM guanine (Tokyo Kasei), 100 mM Tris-hydrochloride buffer (pH 7.5) and 0.1 mL of the ultrasonic enzyme homogenate from a purinenucleoside-phosphorylase producing strain prepared in Example 25 was reacted at 50° C. for 47 hours. To the solution was added calcium chloride to a final concentration of 20 mM and the mixture was reacted at 50° C. for additional 67 hours. HPLC analysis for the post-reaction solution as described in Example 34 showed a peak of 2',3'-dideoxy-3'-fluoro-D-guanosine. A reaction inversion rate was calculated to be 84.4% after determining the concentration of 2',3'-dideoxy-3'-fluoro-D-guanosine in the post-reaction solution.

Example 42

Preparation of 6-chloro-9-(β-D-ribofuranos-1-yl)purine

One mL of a reaction solution consisting of 10 mM 6-chloropurine (Aldrich), 50 mM D-ribose-1-phosphate (22) prepared in Example 10, 0.1 mL of the ultrasonic enzyme homogenate from a purinenucleoside-phosphorylase producing strain prepared in Example 25 and 100 mM Tris-hydrochloride buffer (pH 7.5) was reacted at 50° C. for 20 hours. After completion of the reaction, HPLC analysis for the reaction solution under the conditions described below showed a peak of the title compound. A reaction inversion rate was calculated to be 62.4% after determining the concentration of 6-chloro-9-(β-D-ribofuranos-1-yl)purine in the post-reaction solution.

HPLC Analysis Conditions
   Column: Develosil ODS-MG-5, 250×4.6 mm I.D.
   Column temperature: 40° C.
   Pump flow rate: 1.0 mL/min
   Detection: UV 254 nm
   Eluent: 25 mM potassium dihydrogen phosphate:methanol=75:25 (V/V)

Example 43

Preparation of 1-(2-deoxy-β-D-ribofuranos-1-yl)-1H-imidazo[4,5-b]pyridine and 3-(2-deoxy-β-D-ribofuranos-1-yl)-1H-imidazo[4,5-b]pyridine One mL of a reaction solution consisting of 10 mM 2-deoxy-α-D-ribose-1-phosphate ammonium salt prepared in Example 8, 10 mM 4-azabenzimidazole (Aldrich), 100 mM Tris-hydrochloride buffer (pH 7.5) and 50 µL of the ultrasonic enzyme homogenate from a purinenucleoside-phosphorylase producing strain prepared in Example 25 was reacted at 50° C. for 17 hours. HPLC analysis for the post-reaction solution under the conditions described below showed two peaks of the title compounds. Reaction inversion rates were calculated to be 3% and 7.2% after determining the concentrations of the products in the post-reaction solution.

HPLC Analysis Conditions
   Column: Develosil ODS-MG-5, 250×4.6 mm I.D.
   Column temperature: 40° C.
   Pump flow rate: 1.0 mL/min
   Detection: UV 254 nm
   Eluent: 25 mM potassium dihydrogen phosphate methanol=50:50 (V/V)
   LC-MS analysis data: MS(APCI) m/z: 236 (MH)$^+$ Example 44

Preparation of 8-aza-2'-deoxyadenosine

A reaction was conducted as described in Example 43 except that 8-azaadenine (Aldrich) was used in place of 4-azabenzimidazole. HPLC analysis for the post-reaction solution under the conditions described below showed a peak of 8-aza-2'-deoxyadenosine. A reaction inversion rate was calculated to be 4.8% after determining the concentration of 8-aza-2'-deoxyadenosine in the post-reaction solution.

HPLC Analysis Conditions
   Column: Develosil ODS-MG-5, 250×4.6 mm I.D.
   Column temperature: 40° C.
   Pump flow rate: 1.0 mL/min
   Detection: UV 254 nm Eluent: 25 mM potassium dihydrogen phosphate methanol=875:125 (V/V)

LC-MS analysis data: MS(APCI) m/z: 253 (MH)$^+$

Example 45

Preparation of 8-aza-2'-deoxyguanosine

A reaction was conducted as described in Example 43 except that 8-azaguanine (Tokyo Kasei) was used in place of 4-azabenzimidazole. HPLC analysis for the post-reaction solution as described in Example 44 showed a peak of 8-aza-2'-deoxyguanosine. A reaction inversion rate was calculated to be 36.1% after determining the concentration of 8-aza-2'-deoxyguanosine in the post-reaction solution.

Example 46

Preparation of 2-chloro-2'-deoxyadenosine (Cladribine)

A reaction was conducted as described in Example 43 except that 2-chloro-4-aminopurine was used in place of 4-azabenzimidazole. HPLC analysis for the post-reaction solution under the conditions described below showed a peak of the title compound. A reaction inversion rate was calculated to be 96% after determining the concentration of 2-chloro-2'-deoxyadenosine in the post-reaction solution.

HPLC Analysis Conditions
Column: Develosil ODS-MG-5, 250×4.6 mm I.D.
Column temperature: 40° C.
Pump flow rate: 1.0 mL/min
Detection: UV 254 nm
Eluent: 25 mM potassium dihydrogen phosphate methanol=875:125 (V/V)

Example 47

Preparation of 1-(β-D-ribofuranos-1-yl)-1,3,4-triazole-3-carboxamide (Ribavirine)

A reaction was conducted as described in Example 43 except that 1,2,4-tosyazole-3-carboxamide was used in place of 4-azabenzimidazole. HPLC analysis for the post-reaction solution under the conditions described below showed a peak of the title compound. A reaction inversion rate was calculated to be 69% after determining the concentration of 1-(β-D-ribofuranos-1-yl)-1,3,4-triazole-3-carboxamide in the post-reaction solution.

HPLC Analysis Conditions
Column: Develosil ODS-MG-5, 250×4.6 mm I.D.
Column temperature: 40° C.
Pump flow rate: 1.0 mL/min
Detection: UV 210 nm
Eluent: 25 mM potassium dihydrogen phosphate

Example 48

Preparation of 1-(β-D-ribofuranos-1-yl)-5-aminoimidazole-4-carboxamide (Acadesine)

A reaction was conducted as described in Example 43 except that 5-aminoimidazole-4-carboxamide was used in place of 4-azabenzimidazole. HPLC analysis for the post-reaction solution under the conditions described below showed a peak of the title compound. A reaction inversion rate was calculated to be 46% after determining the concentration of 1-(β-D-ribofuranos-1-yl)-5-aminoimidazole-4-carboxamide in the post-reaction solution.

HPLC Analysis Conditions
Column: Develosil ODS-MG-5, 250×4.6 mm I.D.
Column temperature: 40° C.
Pump flow rate: 1.0 mL/min
Detection: UV 254 nm
Eluent: 25 mM potassium dihydrogen phosphate methanol=93:7 (V/V)

Example 49

Preparation of 2'-deoxyguanosine

To 20 g of purified water were added 3.22 g of 2-deoxyribose-1-phosphate di(monocyclohexylammonium) salt prepared in Example 24 (7.72 mmol), 1.11 g of guanine (7.34 mmol) and 0.67 g of magnesium hydroxide (11.48 mmol). The reaction mixture was adjusted to pH 9 with a 20% aqueous solution of sodium hydroxide. To the mixture was added 0.1 mL of the above enzyme solution (0.1 mL), and the mixture was reacted with stirring at 50° C. for 8 hours. HPLC analysis for the reaction mixture after 8 hours indicated that the desired 2'-deoxyguanosine was provided with a reaction yield of 99%.

Example 50

Preparation of 2'-deoxyadenosine

To 20 g of purified water were added 3.22 g of 2-deoxyribose-1-phosphate di(monocyclohexylammonium) salt prepared in Example 24 (7.72 mmol), 1.01 g of adenine (7.47 mmol) and 0.67 g of magnesium hydroxide (11.48 mmol). The reaction mixture was adjusted to pH 8.6 with a 20% aqueous solution of sodium hydroxide. To the mixture was added 0.1 mL of the above enzyme solution (0.1 mL), and the mixture was reacted with stirring at 50° C. for 3 hours. HPLC analysis for the reaction mixture after 8 hours indicated that the desired 2'-deoxyadenosine was provided with a reaction yield of 99%.

INDUSTRIAL APPLICABILITY

As described above, this invention is quite useful as an anomer selective process for producing a 1-phosphorylated saccharide derivative or a nucleoside and may be expected to used in a variety of applications.

What is claimed is:

1. A process for preparing a nucleoside represented by formula (8):

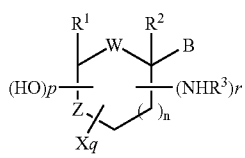

(8)

wherein B is a base independently selected from the group consisting of pyrimidine, purine, azapurine and deazapurine optionally substituted by halogen, alkyl, haloalkyl, alkenyl, haloalkenyl, alkynyl, amino, alkylamino, hydroxy, hydroxyamino, aminoxy, alkoxy, mercapto, alkylmercapto, aryl, aryloxy or cyano;
$R^1$ and $R^2$ independently represent hydrogen, methyl, hydroxymethyl or carboxyl;
$R^3$ represents hydrogen or acyl;
X represents halogen, alkoxy or alkylthio;
W represents oxygen or sulfur;
Z represents oxygen, sulfur or optionally substituted carbon; and
m represents an integer of 1 to 3; n represents 0 or 1; p and q represents an integer of 0 to 4; and r represents 0 or 1; provided that p, q, r and n meet the conditions of $p+r \leq n+1$ and $q \leq 2\times(n+1)-2\times(p+r)$ when Z is oxygen or sulfur and of $p+r \leq n+2$ and $q \leq 2\times(n+2)-2\times(p+r)$ when Z is carbon;
which comprises the steps of:
(a) preparing a 1-phosphorylated saccharide compound monomer represented by formula (3):

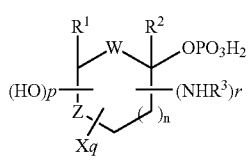

(3)

wherein $R^1$, $R^2$, $R^3$, X, W, Z, n, p, q and r are as defined above, by phosphorolyzing and isomerizing an anomer mixture of a 1-phosphorylated saccharide compound represented by formula (1):

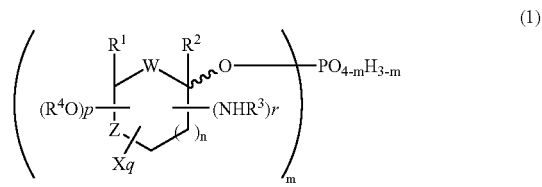

(1)

wherein where $R^1$ and $R^2$ independently represents hydrogen, methyl, protected hydroxymethyl or protected carboxyl; $R^3$ represents acyl; $R^4$ represents a protective group; X, W, Z, m, n, p, q and r are as defined above;
to give α and β isomers of the 1-phosphorylated saccharide compound monomer; selectively crystallizing one of these isomers to displace the equilibrium between these anomers without the use of an enzymatic reaction; and then removing the protective group represented by $R^4$ to obtain the 1-phosphorylated saccharide compound monomer of formula (3); and
(b) conducting an exchange reaction of the phosphate group in the 1-phosphorylated saccharide compound monomer of formula (3) obtained in the step (a) with a base by the action of a nucleoside phosphorylase to obtain the a nucleoside represented by formula (8).

2. A process for preparing a nucleoside as claimed in claim 1, wherein the sugar residue of the compound of formula (3) is not natural.

3. A process for preparing a nucleoside as claimed in claim 1, wherein n is 0.

4. The process for preparing a nucleoside as claimed in claim 3 wherein $R^1$ is hydroxymethyl, $R^2$ is hydrogen, p and r are 0, and X is fluorine.

5. The process for preparing a nucleoside as claimed in claim 3 wherein the nucleoside phosphorylase is at least one enzyme selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

6. The process for preparing a nucleoside as claimed in claim 3 wherein the nucleoside phosphorylase activity is replaced with a microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

7. The process for preparing a nucleoside as claimed in claim 3 wherein a metal cation capable of forming a water-insoluble salt with a phosphate ion is present in the reaction solution during the exchange reaction of a phosphate group in the 1-phosphorylated saccharide derivative monomer with a base by the action of a nucleoside phosphorylase.

8. The process for preparing a nucleoside as claimed in claim 7 wherein the metal cation capable of forming a water-insoluble salt with the phosphate ion is at least one metal cation selected from the group consisting of calcium, barium, aluminum and magnesium ions.

9. A process for preparing a nucleoside as claimed in claim 1, wherein the nucleoside is a natural nucleoside.

10. The process for preparing a nucleoside as claimed in claim 1 wherein the nucleoside phosphorylase is at least one enzyme selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

11. The process for preparing a nucleoside as claimed in claim 1 wherein the nucleoside phosphorylase activity is replaced with a microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

12. The process for preparing a nucleoside as claimed in claim 1 wherein a metal cation capable of forming a water-insoluble salt with a phosphate ion is present in the reaction solution during the exchange reaction of a phosphate group in the 1-phosphorylated saccharide derivative monomer with a base by the action of a nucleoside phosphorylase.

13. The process for preparing a nucleoside as claimed in claim 12 wherein the metal cation capable of forming a water-insoluble salt with the phosphate ion is at least one metal cation selected from the group consisting of calcium, barium, aluminum and magnesium ions.

14. The process for preparing a nucleoside as claimed in claim 2 wherein the nucleoside phosphorylase is at least one enzyme selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

15. The process for preparing a nucleoside as claimed in claim 2 wherein the nucleoside phosphorylase activity is replaced with a microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

16. The process for preparing a nucleoside as claimed in claim 2 wherein a metal cation capable of forming a water-insoluble salt with a phosphate ion is present in the reaction solution during the exchange reaction of a phosphate group in the 1-phosphorylated saccharide derivative monomer with a base by the action of a nucleoside phosphorylase.

17. The process for preparing a nucleoside as claimed in claim 16 wherein the metal cation capable of forming a water-insoluble salt with the phosphate ion is at least one metal cation selected from the group consisting of calcium, barium, aluminum and magnesium ions.

18. A process for preparing a nucleoside represented by formula (21):

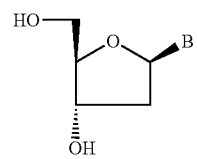

(21)

wherein B is a base independently selected from the group consisting of pyrimidine, purine, azapurine and deazapurine optionally substituted by halogen, alkyl, haloalkyl, alkenyl, haloalkenyl, alkynyl, amino, alkylamino, hydroxy, hydroxyamino, aminoxy, alkoxy, mercapto, alkylmercapto, aryl, aryloxy or cyano, comprising a first procedure of preparing 2-deoxy-α-D-ribose-1-phosphate as claimed in claim 4; and a second procedure of conducting an exchange reaction of the phosphate group in the 1-phosphorylated saccharide compound obtained in the first procedure with a base by the action of a nucleoside phosphorylase.

19. The process for preparing a nucleoside as claimed in claim 4 wherein the nucleoside phosphorylase is at least one enzyme selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

20. The process for preparing a nucleoside as claimed in claim 4 wherein the nucleoside phosphorylase activity is replaced with a microorganism expressing at least one nucleoside phosphorylase selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

21. The process for preparing a nucleoside as claimed in claim 4 wherein a metal cation capable of forming a water-insoluble salt with a phosphate ion is present in the reaction solution during the exchange reaction of a phosphate group in the 1-phosphorylated saccharide derivative monomer with a base by the action of a nucleoside phosphorylase.

22. The process for preparing a nucleoside as claimed in claim 21 wherein the metal cation capable of forming a water-insoluble salt with the phosphate ion is at least one metal cation selected from the group consisting of calcium, barium, aluminum and magnesium ions.

23. The process for preparing a nucleoside as claimed in claim 18 wherein the nucleoside phosphorylase is at least one enzyme selected from the group consisting of purine nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

24. The process for preparing a nucleoside as claimed in claim 18 wherein the nucleoside phosphorylase activity is replaced with a microorganism expressing at least one nucleoside phosphorylase selected from the group consisting of Pu rifle nucleoside phosphorylase (EC2.4.2.1), guanosine nucleoside phosphorylase (EC2.4.2.15), pyrimidine nucleoside phosphorylase (EC2.4.2.2), uridine nucleoside phosphorylase (EC2.4.2.3), thymidine nucleoside phosphorylase (EC2.4.2.4) and deoxyuridine nucleoside phosphorylase (EC2.4.2.23).

25. The process for preparing a nucleoside as claimed in claim 18 wherein a metal cation capable of forming a water-insoluble salt with a phosphate ion is present in the reaction solution during the exchange reaction of a phosphate group in the 1-phosphorylated saccharide compound monomer with a base by the action of a nucleoside phosphorylase.

26. The process for preparing a nucleoside as claimed in claim 25 wherein the metal cation capable of forming a water-insoluble salt with the phosphate ion is at least one metal cation selected from the group consisting of calcium, barium, aluminum and magnesium ions.

* * * * *